US009388402B2

(12) United States Patent
Winge

(10) Patent No.: US 9,388,402 B2
(45) Date of Patent: Jul. 12, 2016

(54) METHOD FOR IMPROVED ISOLATION OF RECOMBINANTLY PRODUCED PROTEINS

(75) Inventor: Stefan Winge, Arsta (SE)

(73) Assignee: Octapharma AG, Lachen (CH)

(*) Notice: Subject to any disclaimer, the term of this patent is extended or adjusted under 35 U.S.C. 154(b) by 1391 days.

(21) Appl. No.: 11/887,677

(22) PCT Filed: Mar. 29, 2006

(86) PCT No.: PCT/EP2006/061148
§ 371 (c)(1),
(2), (4) Date: Feb. 4, 2008

(87) PCT Pub. No.: WO2006/103258
PCT Pub. Date: Oct. 5, 2006

(65) Prior Publication Data
US 2009/0088370 A1 Apr. 2, 2009

(30) Foreign Application Priority Data
Mar. 29, 2005 (EP) .................................. 05102475

(51) Int. Cl.
C07K 14/755 (2006.01)
C12P 21/02 (2006.01)
C12N 9/64 (2006.01)

(52) U.S. Cl.
CPC .............. C12N 9/644 (2013.01); C07K 14/755 (2013.01); C12N 9/647 (2013.01); C12P 21/02 (2013.01); C12Y 304/21022 (2013.01); Y02P 20/52 (2015.11)

(58) Field of Classification Search
None
See application file for complete search history.

(56) References Cited

U.S. PATENT DOCUMENTS

| | | | | |
|---|---|---|---|---|
| 4,770,999 | A | 9/1988 | Kaufman et al. | 435/68 |
| 4,868,112 | A | 9/1989 | Toole, Jr. | 435/68 |
| 4,980,456 | A | 12/1990 | Scandella et al. | 530/383 |
| 5,045,455 | A | 9/1991 | Kuo et al. | 435/69.6 |
| 5,122,469 | A * | 6/1992 | Mather et al. | 435/383 |
| 5,521,070 | A | 5/1996 | Meulien | 435/69.1 |
| 5,789,203 | A | 8/1998 | Chapman et al. | 435/69.6 |
| 5,831,026 | A | 11/1998 | Almstedt et al. | 530/383 |
| 5,851,800 | A | 12/1998 | Adamson | 435/69.1 |
| 6,338,964 | B1 | 1/2002 | Matanguihan | 435/325 |
| 6,897,040 | B2 * | 5/2005 | Morris et al. | 435/69.1 |
| 2002/0012991 | A1 * | 1/2002 | Fong et al. | 435/325 |

FOREIGN PATENT DOCUMENTS

| | | |
|---|---|---|
| EP | 150735 | 8/1985 |
| EP | 160457 | 11/1985 |
| EP | 232112 | 8/1987 |
| EP | 251843 | 1/1988 |
| EP | 253455 | 1/1988 |
| EP | 254076 | 1/1988 |
| EP | 265778 | 5/1988 |
| EP | 294910 | 12/1988 |
| EP | 303540 | 2/1989 |
| EP | 0500734 | 9/1992 |
| WO | WO 86/01961 | 3/1986 |
| WO | WO 86/06101 | 10/1986 |
| WO | WO 87/04187 | 7/1987 |
| WO | WO 87/07144 | 12/1987 |
| WO | WO 88/00381 | 1/1988 |
| WO | WO 91/07490 | 5/1991 |
| WO | WO 91/09122 | 6/1991 |
| WO | WO 95/13300 | 5/1995 |
| WO | WO 00/49147 | 8/2000 |
| WO | WO 01/23527 | 4/2001 |
| WO | WO 01/70968 | 9/2001 |

OTHER PUBLICATIONS

"Cell Harvest Clarification Scaling Strategies" (Retrieved from the Internet <http://www.millipore.com/processdev/pd3/cellharvestscaling>, retrieved on Oct. 13, 2011).*
Schröder et al. (Serum- and protein-free media formulations for the Chinese hamster ovary cell line DUKXB11, Journal of Biotechnology 108 (2004) 279-292).*
International Preliminary Report on Patentability and Written Opinion issued on Mar. 26, 2007 for PCT/GB2009/050115, which published as WO/2006/103258 on Oct. 5, 2006 (Stefan Winge is inventor and Octapharma AG is Applicant).
International Search Report issued on Aug. 18, 2009 for PCT/GB2009/050115, which published as WO/2006/103258 on Oct. 5, 2006 (Stefan Winge is inventor and Octapharma AG is Applicant).
Boedeker BG. (2001) Production processes of licensed recombinant factor VIII preparations. Semin Thromb Hemost. 27(4): 385-394.
Fay PJ, Mastri M, Koszelak ME. (2001) Factor VIIIa cofactor activity shows enhanced ionic strength sensitivity in the absence of phospholipid. Biochim Biophys Acta. 1548(1): 159-168.
Larsson H, Akerud P, Nordling K, Raub-Segall E, Claesson-Welsh L, Björk I. (2001) A novel anti-angiogenic form of antithrombin with retained proteinase binding ability and heparin affinity. J Biol Chem. 276(15):11996-2002.
Kolind MP, Nørby PL, Flintegaard TV, Berchtold MW, Johnsen LB. (2010) The B-domain of Factor VIII reduces cell membrane attachment to host cells under serum free conditions. J Biotechnol. 147(3-4): 198-204.
Mounier CM, Ghomashchi F, Lindsay MR, et al. (2004) Supplementary Material for Arachidonic acid release from mammalian cells transfected with human groups IIA and X secreted phospholipase A(2) occurs predominantly during the secretory process and with the involvement of cytosolic phospholipase A(2)-alpha. Biol Chem. 279(24): 25024-25038.
Spiegel PC, Kaiser SM, Simon JA, Stoddard BL. (2004) Disruption of protein-membrane binding and identification of small-molecule inhibitors of coagulation factor VIII. Chem Biol. 11(10): 1413-1422.

(Continued)

Primary Examiner — Suzanne M Noakes
Assistant Examiner — Jae W Lee
(74) Attorney, Agent, or Firm — Ballard Spahr LLP

(57) ABSTRACT

The present invention provides a method for increasing the yield of a protein produced by cultivating eukaryotic cells and adding an ionic substance to the culture medium prior to harvest of the protein. Suitable ionic substances are the salts of the Hofmeister series, amino acids and peptone.

15 Claims, 4 Drawing Sheets

(56) References Cited

OTHER PUBLICATIONS

Decision to Grant a European Patent pursuant to Article 97(1) EPC issued Nov. 5, 2010 for EP 06725404.5-1212, which was filed on Mar. 29, 2006 (Stefan Winge is inventor and Octapharma AG is Applicant).
Communication under Rule 71(3) EPC issued Jun. 11, 2010 for EP 06725404.5-1212, which was filed on Mar. 29, 2006 (Stefan Winge is inventor and Octapharma AG is Applicant).
Minutes of the Oral Proceedings issued Jun. 4, 2010 for EP 06725404.5-1212, which was filed on Mar. 29, 2006 (Stefan Winge is inventor and Octapharma AG is Applicant).
Brief Communication regarding Oral Proceedings issued May 7, 2010 for EP 06725404.5-1212, which was filed on Mar. 29, 2006 (Stefan Winge is inventor and Octapharma AG is Applicant).
Response to Summons for Oral Proceedings filed Apr. 20, 2010 for EP 06725404.5-1212, which was filed on Mar. 29, 2006 (Stefan Winge is inventor and Octapharma AG is Applicant).
Summons for Oral Proceedings issued Nov. 24, 2009 for EP 06725404.5-1212, which was filed on Mar. 29, 2006 (Stefan Winge is inventor and Octapharma AG is Applicant).
Brief Communication regarding Oral Proceedings issued Nov. 23, 2009 for EP 06725404.5-1212, which was filed on Mar. 29, 2006 (Stefan Winge is inventor and Octapharma AG is Applicant).
Response to Summons for Oral Proceedings filed Oct. 29, 2009 for EP 06725404.5-1212, which was filed on Mar. 29, 2006 (Stefan Winge is inventor and Octapharma AG is Applicant).
Summons for Oral Proceedings issued Sep. 16, 2009 for EP 06725404.5-1212, which was filed on Mar. 29, 2006 (Stefan Winge is inventor and Octapharma AG is Applicant).
Response filed Sep. 22, 2008 for EP 06725404.5-1212, which was filed on Mar. 29, 2006 (Stefan Winge is inventor and Octapharma AG is Applicant).
Communication pursuant to Article 94(3) EPC issued Mar. 13, 2008 for EP 06725404.5-1212, which was filed on Mar. 29, 2006 (Stefan Winge is inventor and Octapharma AG is Applicant).
Demand for International Preliminary Examination filed Jan. 27, 2007 for EP 06725404.5-1212, which was filed on Mar. 29, 2006 (Stefan Winge is inventor and Octapharma AG is Applicant).
Extended European Search Report issued Nov. 4, 2010 for EP 10181018.0-1212, which was filed on Sep. 24, 2010 (Stefan Winge is inventor and Octapharma AG is Applicant).
Boilard E, Bourgoin SG, Bernatchez C, Poubelle PE, Surette ME. (2003) Interaction of low molecular weight group IIA phospholipase A2 with apoptotic human T cells: role of heparan sulfate proteoglycans. FASEB J. 17(9): 1068-1080.
Berman, K. et al., "Isolation and Characterization of pmk-(1-3): Three p38 Homologs in Caenorhabditis elegans" Mol. Cell Biol. Res. Com. 4, 337-344 (2001).
Chen, C. et al., "High-Efficiency Transformation of Mammalian Cells by Plasid DNA" Mol. Cell Biol. 7(8), 2745-2752 (1987).
Denys, A. et al., "Involvement of two classes of binding sites in the interactions of cyclophilin B with peripheral blood T-lymphocytes" Biochem J., 336, 689-697 (1998).
Dey, P.M. et al., "Extensin from suspension-cultured potato cells: a hydroxyproline-rich glycoprotein, devoid of agglutinin activity" Planta 202: 179-187.
Eriksson et al., "The Manufacturing Process for B-Domain Deleted Recombinant Factor VIII" Seminars in Hematology 38, Suppl. 4, 24-31 (2001).
Fannon, M. et al., "Potentiation and Inhibition of bFGF Binding by Heparin: A Model for Regulation of Cellular Response" Biochemistry 39, 1434-1445 (2000).
Fuire and Furie, "The Molecular Basis of Blood Coagulation" Cell (1988) 53, 505-518.
Graham, F.L., "Characteristics of a Human Cell Line Transformed by DNA from Human Adenovirus Type 5" J. Gen Virol. 36(1), 59-74 (1974).
Grasser et al., "Camelysin Is a Novel Surface Metalloproteinase from *Bacillus cereus*" Infection and Immunity. p. 213-228 (2004).
Herlitschka et al., High expression of a B-domain deleted factor VIII gene in a human hepatic cell line Journal of Biotechnology 61, 165-173 (1998).
Mounier et al., "Arachidonic Acid Release from Mammalian Cells Transfected with Human Groups IIA and X Secreted Phospholipase $A_2$ Occurs Predominantly during the Secretory Process and with the Involvement of Cytosolic Phospholipase $A_2$-$\alpha$" J. Biol. Chem. 279, No. 24, pp. 25024-25038 (2004).
Norbeck, J. et al., Proein expression during exponential growth in 0.7 M NaCI medium of *Sacchatomyces cerevisiae* FEMS Microbiology Letters 137, p. 108 (1996).
Sandberg et al., "Structural and Functional Characterization of B-Domain Deleted Recombinant Factor VIII" Seminars in Hematology 38, Suppl 4, 24-31 (2001).
Vaandrager et al., "N-terminal Myristoylation Is Required for Membrane Localization of cGMP-dependent Protein Kinase Type II" J. Biol. Chem., vol. 271, No. 12, pp. 7025-7029 (1996).
Wang et al., "Coagulation factor VIII: structure and stability" International Journal of Pharmaceutics 259, 1-15 (2003).
Zuber et al., "Cysteine-Rich FGF Receptor Regulates Intracellular FGF-1 and FGF-2 Levels" J. Cell Physiology, 170:217-227 (1997).
Adamson R. (1994) Design and operation of a recombinant mammalian cell manufacturing process for rFVIII. Ann Hematol. 68 Suppl 3:S9-S14.
Fang H, et al. (2007) The protein structure and effect of factor VIII. Thromb Res. 119(1):1-13.
Fuentes-Prior P, et al. (2002) New insights into binding interfaces of coagulation factors V and VIII and their homologues lessons from high resolution crystal structures. Curr Protein Pept Sci. 3(3):313-339.
Pratt KP, et al. (1999) Structure of the C2 domain of human factor VIII at 1.5 A resolution. Nature. 402(6760):439-442.
Spiegel PC Jr, et al. (2001) Structure of a factor VIII C2 domain-immunoglobulin G4kappa Fab complex: identification of an inhibitory antibody epitope on the surface of factor VIII. Blood. 98(1):13-19.
"Chapter 6—The Plasma Membrane" in *Molecular Biology of the Cell*, $2^{nd}$ Edition (Bruce Alberts, et al., Eds.; Published in New York, New York, 1989), pp. 284-285.
"Chapter 12—Protein Conformation, Dynamics, and Function" in *Biochemistry*, $3^{rd}$ Edition (Lubert Stryer, Ed.); Published in USA, 1988); pp. 292-293.
"Chapter 11—The Molecular Biology of Blood Coagulation" in *Current Hematology*, vol. 2 (Virgil F. Fairbanks, Ed.); Published in USA, 1983, pp. 347-374.
"Chapter 29—Extraction of Membrane Proteins" in *Methods in Molecular Biology*, vol. 244—Protein Purification Protocols, $2^{nd}$ Edition (P. Cutler, Ed.); 2003, pp. 283-293.
"Chapter 3—Protein Structure and Function" in *Molecular Cell Biology*, $4^{th}$ Edition (Harvey Lodish, et al., Eds.); Published in the USA, 1999; pp. 82-85.
"E2—Membrane Protein and Carbohydrate" in *Biochemistry*, $3^{rd}$ Edition (David Hames, et al., Eds.); Published in USA, 2005, pp. 124-129.

* cited by examiner

Initiation Phase:

A — Recovery of cell bank: revitalization of cryovial in T-flask

B — Transfer into shaker bottle culture

Production Phase:

D — Inoculation in 5L cell culture volume anexpansioto production cell density

D (Harvest) — Fermentation: Production repeated batch mode

Harvest by centrifugation or Filtration

Fig. 1

METHOD FOR IMPROVED ISOLATION OF RECOMBINANTLY PRODUCED PROTEINS

CROSS REFERENCE TO RELATED APPLICATIONS

The present application is a National Phase Application of International Application No. PCT/EP2006/061148, filed Mar. 29, 2006, which claims priority to European Patent Application No. 05102475.0, filed Mar. 29, 2005, which applications are incorporated herein fully by this reference.

The present invention provides a method for increasing the yield of a protein produced by cultivating eukaryotic cells under serum-free conditions and adding an ionic substance to the culture medium prior to harvest of the protein. Suitable ionic substances are the salts of the Hofmeister series, amino acids and peptone.

BACKGROUND

Most proteins for medical, cosmetic or industrial applications are produced as recombinant proteins in cultivated microbial or eukaryotic cells. For that a gene encoding the protein of interest is inserted into the organism/cells of choice, the organism/cells carrying said gene is cultivated in a medium comprising all essential nutrients to allow for growth and expression of said gene, resulting in the production of the protein of interest. If the protein of interest is secreted by the cells into the medium, the cells and the medium are separated from each other using centrifugation or filter membranes. The recovered cell-free protein containing medium is then further processed through purification steps to remove host cell proteins, DNA and other contaminants.

In general, there are two different production alternatives for the harvest of recombinantly produced proteins, continuous and batch harvest. When applying continuous harvest, the cultivation media is continuously slowly removed from the cell cultivation vessel during the production phase and fresh medium is simultaneously added. Continuous harvest is chosen when the cells are slowly growing and/or the process facilitates a high cell concentration or if the product must be removed fast from the cultivation to protect it from degradation. Batch harvesting is performed at one defined point, where the cells are removed in one step and thereafter they are normally discarded. It is technically easier to run a batch harvesting compared to a continuous one, but the optimal harvest procedure must be determined in each specific case depending on product and cell type. In some cases, where the product is not secreted, the cell membrane must be destroyed in order to recover the product. It is, however, preferred to keep the cell membrane intact, if possible, in order to avoid contamination of the product with DNA and host cell proteins. Continuous harvest normally gives a higher total productivity compared to batch harvest as the cells can produce for a longer period of time. To minimize the contamination of the product, it is preferable to choose the harvest method which releases the lowest amount of DNA and host cell proteins. In a special mode of batch harvesting, where the cell membranes are kept intact, a considerable improvement in productivity can be achieved, if the cell can be reused. This cyclic batch harvest method is particularly applicable for slowly growing (valuable) production cells.

To obtain high yields of the protein, it is important to optimize the process to achieve a high productivity of the product. The main efforts so far to improve the yield of a recombinantly produced protein have focused on the molecular insert (vectors, enhancers, promoters, etc.) to optimize the expression system, the conditions under which the cells are cultured and the actual purification steps. For example stabilizers such as protease inhibitors are added into the medium and the purification procedures are set up in the presence of protease inhibitors to reduce the loss of the product protein. However, it is often very difficult to find a protease inhibitor which can be used during cultivation, as protease inhibitors also tend to inhibit cell growth and protein production. As soon as the cells have been removed, it is easier to find a suitable protease inhibitor. This is described, for example, in U.S. Pat. No. 5,831,026, where EDTA is added to inhibit metallo-proteases. Moreover, it is to be noted that any stabilizing agents added need to be removed again at some point of the production process to obtain a pure recombinant protein product. Thus there is still a need to improve the existing methods of recombinant protein production to gain higher yields of the recombinant protein.

Another problem encountered especially when utilizing mammalian cells as production hosts is that the secretion of the produced proteins is rather low. It is apparent that secreted products often adhere to the cell membrane and that this has an influence on the product release. In some cases, the retardation can be inhibited by physiological conditions (i.e. the environment in which the cells are cultivated), whereas in some cases non-physiological conditions must be applied. The total disruption of cells should be avoided, if possible, as this releases DNA and host cell proteins, which need to be removed later in the purification process.

It is known in the art that an increase in salt concentrations (for instance, NaCl), accompanied by the addition of detergent and/or by adjusting a specific pH can in some cases release the bound proteins. For instance, K. Berman et al., Mol. Cell Biol. Res. Com. 4, 337-344 (2001) emphasizes that in the production of p38 homologs in HEK293 cells, the cells could be stimulated with sorbitol or 0.7 M NaCl for 10 minutes prior to harvest. A. B. Vaandrager et al., J. Biol. Chem., Vol. 271, No. 12, pp. 7025-7029 (1996) discloses that the cultivation of HEK293 cells expressing rat cGKII resulted in recovery of 90-95% of the expressed cGKII, and that the enzyme could be released from membranes by a combination of detergent (1% Triton® X-100) and high salt (0.5 M NaCl) but not by detergent or high salt alone. A. Denys et al., Biochem J., 336, 689-697 (1998) disclose that a protein was released from human T-lymphocyte cells using a washing procedure including 0.6 M NaCl. However, not all (70%) protein could be released even if NaCl concentration was raised to 1 M. Moreover, low pH, such as pH 4 did not release all of the bound protein (34%), while a combination of low pH and increased salt concentration (0.5 M NaCl, 0.2 M glycine, pH 4) released all bound protein. G. Grass et al., Infection and Immunity, p. 213-228 (2004) discloses that in the bacterial expression of metalloproteinases, the washing procedure with high ionic strength buffer (3 M NaCl) did not release the protein. The protein could, however be released by butanol or a detergent. C. M. Mounier et al., J. Biol. Chem. 279, No. 24, pp. 25024-25038 (2004) reports for HEK293 and CHO cells that proteins expressed by said cells bind to the cell surface. This could be inhibited by increased salt concentration (NaCl) in the range of 0.12 to 1 M. At 1 M all proteins seemed to be released. In one example with HEK293 the cells were treated with 1 M NaCl and the released protein increased three times. M. Fannon et al., Biochemistry 39, 1434-1445 (2000) reports on the binding of proteins to fibroblasts. Three different washing procedures were compared, high salt (2 M NaCl, pH 7.4), low pH (20 mM sodium acetate, pH 4) and high salt, low pH (2 M NaCl, pH 4). All buffers do under certain circumstances release the protein. High salt and low pH is effective in all experiments. M. E. Zuber et al., J. Cell Physiology, 170:217-227 (1997) reports that the protein binding to the surface of CHO cells could be inhibited by high salt/low pH treatment (2 M NaCl, pH 4). J. Norbeck et al., FEMS Microbiology Letters 137, p. 1-8 (1996) reports about yeast cells which were subjected for 0.4 M NaCl for a period of 1.5 h during growing and about the effects thereof on the expression rate of various proteins. Finally, P. M. Dey et al., Planta 202:179-187 reports on the isolation of hydroxyproline-rich glycopoteins from suspension-cultured potato cells by washing the potato cells with a solution containing 50 mM $CaCl_2$ and 2 mM ascorbic acid.

In view of the above it is apparent that a general method to increase the recovery of recombinant proteins in eukaryotic or mammalian expression systems is still desirable. Of particular interest are methods for the serum-free production of proteins which are needed for medical applications (such as plasma proteins including blood clotting factors which are required for the treatment of hemophilic disorders) and for which the serum-free product is desirable for obvious reasons. Hemophiliacs are suffering from hemorrhagic morbidity caused by the disturbed function of protein components of the blood coagulation cascade. Depending on the affected clotting factor, the hemophilia is classified in two types, hemophilia A and B, in both of which the conversion of soluble fibrinogen to an insoluble fibrin-clot is inhibited. They are recessive X-chromosomally-linked genetic disorders affecting mainly the male population.

Hemophilia A affects 1-2 individuals per 10.000 males. This is a genetic disorder that affects the ability of the blood to form an effective clot and thereby results in prolonged bleeding. As hemophilia A is an X-chromosome linked recessive disorder, almost exclusively men are affected. It is caused by the deficiency or absence of factor VIII, a very large glycoprotein (Mr approximately 330 kDa (Furie B., Furie B. C., Cell (1988) 53, 505-518; the sequence thereof is given in SEQ ID NO:2)), which represents an important element of the blood coagulation cascade. The polypeptide sequence of FVIII can be subdivided in three regions, an N-terminal region consisting of the so-called A1 and A2-domains, a central B-domain region and a C-terminal region composed of the A3, C1 and C2 domains. In the blood coagulation factor VIII occurs as an inactive precursor. It is bound tightly and non-covalently to von Willebrand Factor (vWF), which acts as a stabilizing carrier protein. Proteolytical cleavage of factor VIII by thrombin at three specific positions (740, 1372, 1689; see SEQ ID NO:2) leads to its dissociation from vWF and releases the procoagulant function within the cascade. In its active form factor VIII functions as a cofactor for factor IXa, thereby accelerating the proteolytic activation of factor X by several orders of magnitude.

Hemophilia B occurs in about 1 of 25,000 males. It is characterized by a deficiency of the serine protease factor IX (Christmas factor; see SEQ ID NO:11). The gene encoding factor IX is localized on the X-chromosome (locus Xq27) making hemophilia B an X-chromosome linked recessive disorder. This 415 amino-acid polypeptide is synthesized in the liver as a 56 kDa glycoprotein. In order to attain its proper function a posttranslational carboxylation step is required which only occurs in the presence of vitamin K.

Treatment of these types of bleeding disorders traditionally involves infusions of human plasma-derived protein concentrates of the missing factor(s), i.e. replacement therapy. Although this method represents an efficient therapy for hemophiliacs, it carries the risk of transmission of various infectious agents, such as viruses causing hepatitis or AIDS, or thromboembolic factors. Alternatively several recombinant DNA techniques for the production of clotting factors have been described. The corresponding cDNAs of wild type factor VIII and factor IX have been isolated and cloned into suitable expression vectors (EP-A-160457; WO-A-86/01961, U.S. Pat. Nos. 4,770,999, 5,521,070 and 5,521,070).

In the case of factor VIII, recombinant expression of subunits for the production of complexes showing coagulant activity is known in the art (e.g., from EP-A-150735, EP-A-232112, EP-A-0500734, WO-91/07490, WO-95/13300 U.S. Pat. Nos. 5,045,455 and 5,789,203). Moreover, the expression of truncated cDNA-versions partially or entirely lacking the sequence coding for the highly glycosylated B-domain have been described (e.g. in WO-86/06101, WO-87/04187, WO-87/07144, WO-88/00381, EP-A-251843, EP-A-253455, EP-A-254076, U.S. Pat. Nos. 4,868,112 and 4,980,456, EP-A-294910, EP-A-265778, EP-A-303540, WO-91/09122 and WO 01/70968).

The following passages provide details on human factor VIII because it was chosen as a model recombinant protein to illustrate the present invention.

The gene encoding the factor VIII protein is situated at the tip of the long arm of the X chromosome on locus Xq28. It spans over 186 kb, and thus is one of the largest genes known. The factor VIII gene comprises 26 exons and its transcription and subsequent processing results in a 9-kb mRNA. Translation of this mRNA leads to a polypeptide chain of 2351 amino acids, containing a signal peptide of 19 and a mature protein of 2332 amino acids (see SEQ ID NOs:1 and 2). Analysis of the primary structure determined from the cloned factor VIII cDNA revealed the organization in structural domains occurring in the order A1-a1-A2-a2-B-a3-A3-C1-C2.

The short spacers a1, a2 and a3 are so-called acidic regions containing clusters of Asp and Glu residues and are in literature often included in the A-domains resulting in the slightly simplified domain structure A1-A2-B-A3-C1-C2. Following translation and posttranslational modification, the primary translation product, having a molecular mass of approximately 300 kDa, undergoes intracellular proteolysis when leaving the Golgi apparatus processing the primary translation product into an amino terminal heavy chain of 90-210 kDa (A1-a1-A2-a2-B) and a carboxy terminal light chain of 80 kDa (a3-A3-C1-C2), giving rise to the heterodimeric molecule circulating in blood plasma. In this heterodimeric molecule the heavy and light chain of factor VIII are noncovalently linked by divalent metal ions. The span in molecular weights of the heavy chain is the result of different degrees of proteolytic cleavage of the B-domain. The more or less truncated B-domain remains attached to the A2-domain. The B-domain does not seem to have an influence on the biological activity of the FVIII molecule. This is supported by the fact that during activation of the FVIII the entire B-domain is cleaved off. Immediately after its release into the bloodstream, the FVIII heterodimer interacts with a carrier protein called "von Willebrand factor" (vWF). This interaction stabilizes the heterodimeric structure of FVIII increasing the half-life of FVIII in the blood circulation. Furthermore the complex-formation with vWF prevents the premature binding of factor VIII to cell membranes and components of the tenase complex. Also proteolytic cleavage of the FVIII molecule is to some extent prevented with the molecule being non-covalently bound to vWF. However, thrombin cleavage of FVIII is still possible and results in a loss of affinity to vWF and the conversion of FVIII to its active form.

As could be seen in the preceeding paragraph, factor VIII is a complex glycoprotein resulting in a difficult production process to maintain structural integrity and stability of the protein. Especially the B-domain harboring totally 19 of the altogether 25 N-linked glycosylation sites makes manufacturing of the full length protein difficult, as incorrect glycosylation always bears the risk of immunogenic reactions against the product. The function of the B-domain is not completely elucidated yet, but it has been found that this domain is not essential for the haemostatic function of factor VIII (Sandberg et al., Seminars in Hematology 38, Suppl 4, 24-31 (2001). This observation has been made both in vitro and in vivo for human plasma-derived factor VIII that lacks the entire B-domain, as well as for multiple forms of recombinant factor VIII molecules lacking the entire B-domain. Plasma-derived B-domain deleted factor VIII can be purified from plasma-derived factor VIII concentrates as these concentrates contain multiple active forms of factor VIII ranging in size from 170 kDa to 280 kDa most likely resulting from differences in the length of the B-domain still contained in the heterodimeric protein, supporting the finding that the B-domain is not essential for the biological activity of factor VIII (Eriksson et al., Seminars in Hematology 38, Suppl. 4, 24-31 (2001). In addition to its increased structural stability, transfection of eukaryotic cells with cDNA of the B-domain deleted factor VIII also yielded improved expression levels of the protein (Herlitschka et al., Journal of Biotechnology 61, 165-173 (1998)). These features resulted in one B-domain deleted recombinant factor VIII product being available on the market, showing comparable safety and efficacy as full length recombinant and plasma-derived factor VIII.

Generally deletion of the B-domain has been done on the cDNA-level resulting in the reduction of the overall size of the full-length factor VIII molecule by approximately 40% from 2332 amino acids to 1440 amino acids. The C-terminus of the heavy chain and the N-terminus of the light chain has in some cases been joined using a short amino acid linker replacing the entire B-domain with its 908 amino acids such in WO 00/49147 and WO 01/70968). The N-terminus of the linker described in these references was derived from the N-terminus of the B-domain whereas the C-terminus consists of a specially designed linker sequence. Like the full length recombinant factor VIII and the plasma-derived factor VIII, the majority of the B-domain deleted factor VIII is secreted as a non-covalently linked heterodimer of the heavy and the light chain. Also a small amount of non-cleaved single chain B-domain deleted recombinant factor VIII with a molecular weight of 170 kDa is secreted. Extensive studies have shown that binding to von Willebrand factor and activation by thrombin cleavage as well as interaction with several other physiologically relevant molecules is comparable to that described for the natural human factor VIII.

Recombinant factor VIII products exist. As the abundance of mRNA transcripts is very low (only $10^{-5}$ of the total mRNA of the liver) it took long to obtain the complete cDNA transcript of the protein. With this major breakthrough in the 1980s and the successful transfection of CHO cells with the cDNA, the first recombinant factor VIII product was introduced to the market in 1992. Since then, the annual sales of recombinant factor VIII preparations have reached values >1 billion US$ (Schmid: Pocket Guide to biotechnology and genetic engineering; Wiley-VCH (2003)). Currently four different recombinant factor VIII preparations are available on the market. The manufacturers of these four preparations cover approximately 60% of the demand for factor VIII preparations in the developed countries. However, capacity is still not sufficient and methods to increase the yield of a production process for a recombinant protein will be particularly beneficial for the production of recombinant factor VIII.

In the production of a recombinant B-domain deleted FVIII according to WO 01/70968, HEK cells were transformed with a gene for FVIII, transformed cells were cultivated and FVIII was secreted. During the harvest of the cells, the FVIII molecule and the cells were separated using centrifugation or filter membranes. The recovered cell-free FVIII containing media was then further processed through purification steps to remove host cell proteins, DNA and other contaminants. The recovery rates of the expressed FVIII obtained so far were only moderate.

In general and specifically for the recombinant production of proteins (including plasma proteins such as FVIII), it is very important to optimize the process to achieve a high productivity of the product. This is essential for the economy of the product as the recombinant production procedure is relatively expensive and sensitive for disturbances (infections, etc.) due to its biological origin.

SUMMARY OF THE INVENTION

In view of the above, it is desirable to establish a serum-free production method providing increased yields of recombinant protein. Surprisingly it was found that by a very simple measure, the yield of a recombinant protein to be harvested from the serum-free culture medium can be increased approximately 2 to 20-fold. Thus, the present invention provides a method to improve the yield of recombinant proteins produced by cultivating eukaryotic cells under serum-free conditions. In more detail, the present invention provides:

(1) a method for the recombinant production of at least one target protein in eukaryotic cells, which comprises effecting cultivation of eukaryotic cells, being capable of expression of said at least one target protein, under serum-free conditions and subjecting a suspension of said cells, prior to separation of the protein from the cells, to a non-physiologically increased concentration of at least one ionic substance;

(2) a preferred mode of the method according to embodiment (1), wherein said at least one ionic substance is a salt, an amino acid or a mixture of peptides and/or amino acids, preferably the salt is an alkaline or alkaline earth metal salt such as a salt of the Hofmeister series, the amino acid is an amino acid with charged R-group, and the mixture of peptides and amino acids is a peptone;

(3) a preferred mode of the method according to embodiment (1) or (2), which comprises one or more of the following steps:
  (a) cultivating the cells in a culture medium;
  (b) separating the culture medium from the cultivated cells, resulting in two separate fractions, a fraction of cultivated cells and a fraction of liquid medium;
  (c) contacting or suspending the fraction of cultivated cells with a release composition comprising a non-physiologically increased concentration of at least one ionic substance as defined in (1) or (2) above;
  (d) removing the culture medium from the cells, resulting in two separate fractions, a fraction of cells and a fraction of release composition;
  (e) isolating the plasma protein from the fraction of the release composition; and
  (f) suspending the fraction of cells of (d) above in culture medium and reculture; and (4) a protein composition or a pharmaceutical composition obtainable by the methods (1) to (3) as defined above.

The gist of the present invention resides in the use of an ionic substance, which is added to the cell suspension (or directly the culture medium) immediately prior to harvest. The addition of the ionic substance to the cell suspension allows both disruptive isolation methods (where the cells are destroyed) and methods where the desired protein is secreted.

In case of the latter the method may be adapted to a cyclic process, after subjecting the cell suspension to the increased ionic substance, separation of the suspension into cell fraction and liquid fraction and isolation of a desired protein from the liquid fraction, the cell fraction may be recultured, e.g. as specified in embodiment (3) above.

BRIEF DESCRIPTION OF THE FIGURES

FIG. 1: Scheme showing a cultivation procedure.

FIG. 3A (Western Blot method 1): lane 1: Molecular mass marker (SeeBlue); lane 2: Standard rFVIII (Refacto, Wyeth), 200 IU/ml; lane 3: rFVIII from a release procedure using 0.1 M NaCl (Example 6A), 9 IU/ml; lane 4: rFVIII from a release procedure using 0.55 M NaCl, 18 IU/ml (Example 6D); lane 5: rFVIII from a release procedure using 0.55 M NaCl, 16 IU/ml (Example 6A); lane 6: rFVIII from a release procedure using 0.55 M NaCl, 13.6 IU/ml (Example 7B)

FIG. 3B (Western Blot method 2, high sensitivity: lane 1: Molecular mass marker; lane 2: Reference cell suspension FVIII 1 IU/ml; lane 3: Reference cell suspension FVIII 0.2 IU/ml; lane 4: rFVIII from a release procedure using 0.2 M $CaCl_2$, 1.6 IU/ml (Example 6A); lane 5: rFVIII from a release procedure using 0.2 M $CaCl_2$, 0.73 IU/ml (Example 6A); lane 6: rFVIII from a release procedure using 0.1 M $CaCl_2$, 1.73 IU/ml (Example 8A); lane 7: rFVIII from a release procedure using 0.1 M $CaCl_2$, 0.87 IU/ml (Example 8A); lane 8: rFVIII from a release procedure using 0.55 M NaCl, 1.81 IU/ml (Example 6A).

DETAILED DESCRIPTION OF INVENTION

Figure 2:
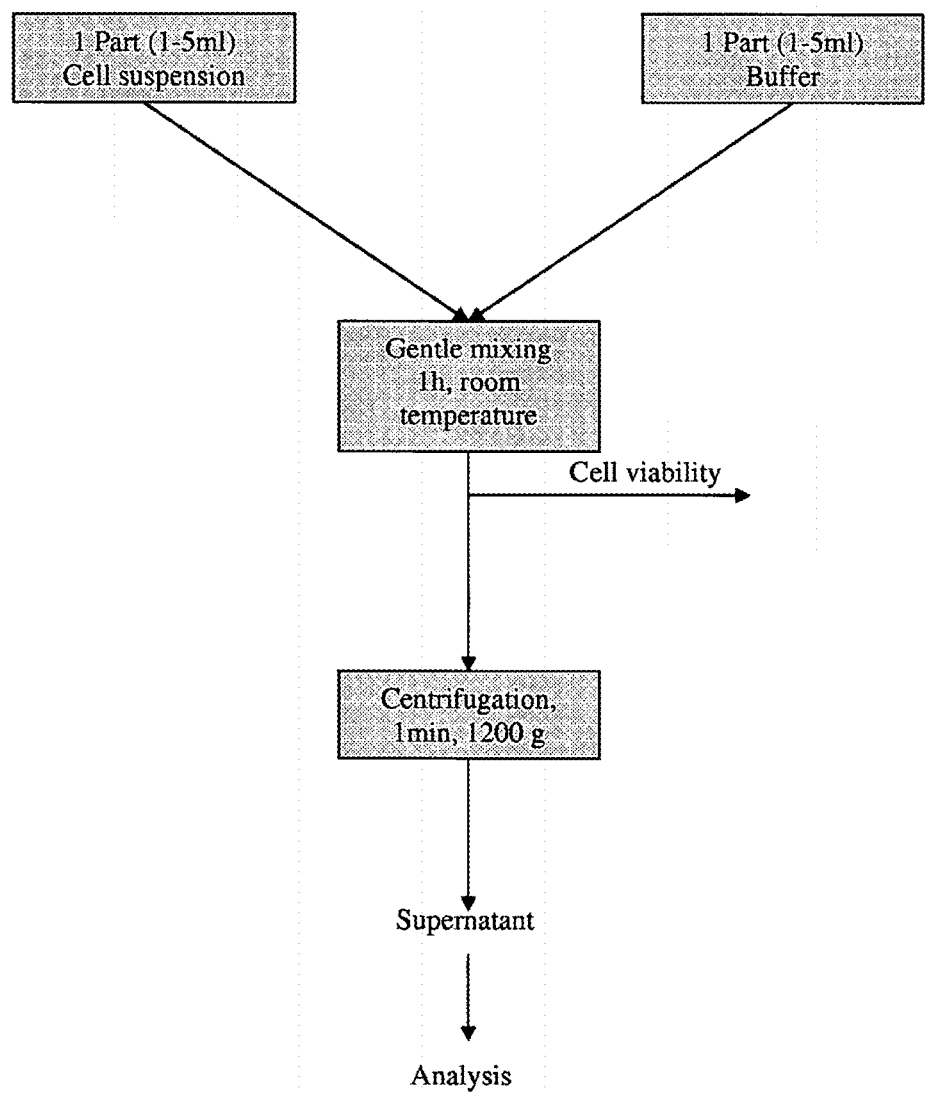
FIG. 2: Flow chart of the experimental set up for small scale experiments. First, the cell suspension and the ionic substance in liquid form (buffer) are mixed and incubated for 1 h at room temperature. Following the incubation the viability of the cells is checked, before the cells are separated from the medium via centrifugation. The supernatant (cell free medium) is then analysed for the recombinant protein or frozen for later analysis.

The term "yield" within the meaning of the invention is defined as the change in release of FVIII compared with the yield obtained using normal harvest procedures (harvest without addition of charged substances) or compared with harvest procedures with addition of physiological salt levels or lower, typical 0.1 M NaCl was added to the cell culture medium.

The term "serum-free" refers to the transfection and culturing of cells in medium containing suitable supplements except any kind of serum. Supplements are selected from amino acids, lipids, trace elements, vitamins and other growth enhancing components. Often the "serum-free" culture conditions are even more stringent and, if no exogenous protein is added, or already included in the medium, the medium is called "protein-free".

The term "protein" includes naturally synthesized proteins which are encoded by genes of the cultivated cell as well as recombinant proteins secreted by cells. Recombinant proteins are those which are encoded by transgenes introduced into the cells by molecular biology techniques. In accordance with the invention, "protein" includes proteins of human and animal origin, but also proteins of other sources such as plants, insects, etc., and mutated, artificial, synthetic, fusion or chimeric proteins. In particular "protein" includes plasma proteins, peptide hormones, growth factors, cytokines and antibodies. In more detail, plasma proteins include human and animal blood clotting factors such as fibrinogen, prothrombin, thrombin, FX, FXa, FIX, FIXa, FVII, FVIIa, FVIII, FVIIIa, FXI, FXIa, FXII, FXIIa, FXIII, FXIIIa, von Willebrand factor etc., transport proteins such as albumin, transferrin, ceruloplasmin, haptoglobin, hemoglobin, hemopexin, etc., protease inhibitors such as β-antithrombin, α-antithrombin, α2-macroglobulin, C1-inhibitor, tissue factor pathway inhibitor (TFPI), heparin cofactor II, protein C inhibitor (PAI-3), Protein C, Protein S, etc., antiangionetic proteins such as latent-antithrombin, etc., highly glycosylated proteins including alfa-1-acid glycoprotein, antichymotrypsin, inter-α-trypsin inhibitor, α-2-HS glycoprotein, C-reactive protein, etc. and other proteins such as histidine-rich glycoprotein, mannan binding lectin, C4-binding protein, fibronectin, GC-globulin, plasminogen, blood factors such as erythropoietin, interferon, tumor factors, tPA, gCSF and derivatives and muteins thereof. Preferably the plasma protein is a human factor VIII protein (see SEQ ID NO:2 for the full length protein) or a human factor IX protein (see SEQ ID NO:11 for the full length protein) or muteins thereof. A mutein of the human factor VIII protein is e.g., a B-domain deleted factor VIII protein.

A particular factor VIII mutein in which the B-domain between positions Arg740 and Glu1649 has been replaced by an Arg-rich linker peptide having at least 3 Arg residues and comprising 10 to 25 amino acid residues (wherein said factor VIII numbering is relative to the mature wild-type factor VIII sequence shown in SEQ ID NO:2) is disclosed in WO 01/70968 which is herewith incorporated in its entirety. It is preferred that the Arg-rich linker peptide has 14 to 20 amino acid residues, while a linker comprising:

the amino acid sequence SFSQNSRH (SEQ ID NO:7), and/or the amino acid sequence QAYRYRRG (SEQ ID NO:8), and/or the amino acid sequence SFSQNSRHQAYRYRRG (SEQ ID NO:9)

is particularly preferred. Most preferred is a factor VIII mutein, which comprises amino acids 1 to 1440 of SEQ ID NO:4, or even more, a factor VIII mutein having SEQ ID NO:4.

The factor VIII protein or factor VIII mutein as defined hereinbefore may have one or more of the following (additional) mutations (a), (b) and (c):

(a) Val at position 162 has been replaced by a neutral amino acid residue selected from Gly, Ala, Leu, Ile, Met and Pro;

(b) Ser at position 2011 has been replaced by a hydrophilic amino acid residue selected from Asn, Thr and Gln; and (c) Val at position 2223 has been replaced by an acidic amino acid residue selected from Glu and Asp (again said factor VIII numbering is relative to the mature wild-type factor VIII sequence shown in SEQ ID NO:2).

Preferred is a factor VIII protein or factor VIII mutein that has at least one of the mutations (a) and (b) or has all three mutations (a), (b) and (c).

Furthermore, preferred mutations in (a) to (c) are the following: (a) Val at position 162 has been replaced by Ala, (b)

Ser at position 2011 has been replaced by Asn, and/or (c) Val at position 2223 has been replaced by Glu.

Particularly preferred is a factor VIII mutein, which comprises amino acids 1 to 1440 of SEQ ID NO:6, or even more, a factor VIII mutein having SEQ ID NO:6

There is no limitation on the vectors for the expression of the proteins of the invention. Suitable vectors include vectors of the pUC series, such as pUC19 (MBI Fermentas) and modifications thereof as utilized in WO 01/70968, which is herewith incorporated in its entirety. The vectors for the particularly preferred factor VIII muteins mentioned hereinbefore, are pTGF8-3 and pTGF8-2hyg-s, the structure of which being shown in FIG. 4 and the exact DNA sequences thereof being given in SEQ ID NOs:3 and 5, respectively. The preparation of said vectors is disclosed in WO 01/70968.

A further preferred plasma protein is factor IX or a mutein thereof, preferably is wild-type human factor IX shown in SEQ ID NO: 11. Suitable muteins of factor IX include point mutated and truncated forms of the factor IX. Vectors for expression of factor IX, such as pTGFG36hyg and pTGFG36 (the 5753 bps circular DNA of the latter being given in SEQ ID NO: 10; bases 689-2071 within SEQ ID NO: 10 coding for the factor IX protein) are disclosed in WO 01/70968.

The terms "eukaryotic cells" and "eukaryotic cell" according to the invention include isolated cells or isolated tissue of multicellular organisms such as vertebrates (including mammals (viz. humans, rodents, etc.), fish, etc.), invertebrates (including insects, worms, etc.) and plants (higher plants, algae, fungi, etc.); or can be lower eukaryotic cells such as yeasts, etc. Particularly preferred eukaryotic cells for the present invention are mammalian cells including animal and human cells which are kept in culture medium. Particularly preferred for the production of human proteins such as human plasma proteins are human cells such as primary cells or immortalized cells such as kidney, bladder, lung, liver, cardiac muscle, smooth muscle, ovary or gastrointestinary cell. Most preferred are human foetal kidney cells such as 293 (DSM ACC 305), 293T (DSM ACC 2494), and 293F and 293H (Invitrogen 11625-019 and 11631-017, respectively) etc. Other particularly suitable cells are Cos, CHO, hybridoma, myeloma such as NS0 cells and insect cells. Particularly preferred are cells out of the above, which are adapted to be cultivated under serum-free conditions.

In a preferred embodiment the mammalian cells, including those mentioned above are stably transfected with an expression cassette carrying the gene coding for the protein or plasma protein.

The increasing (adjusting) of the concentration of the ionic substance in the cell suspension is effected by adding to the cell suspension a release composition comprising said at least one ionic substance. The release composition can be added to the cell suspension in solid or liquid form. It is, however, preferred that the release composition is being added to the cell suspension up to 72 h, preferably 12-24 h and most preferable 1 to 120 min prior to the separation of the protein. In a preferred mode of the method of the invention the release composition is directly added to the culture broth or added to the cells or to a suspension of the cells isolated from the culture broth. The release composition may be added in one step or may be gradually added to reach the final concentration within 1-4300 minutes. The release composition may also be added with diafiltration technique.

"Non-physiologically increased concentration of an ionic substance" refers to a concentration of the ionic substrate which is higher than the concentration in the cell/in the optional culture medium of the cell at normal conditions (for example in vitro).

The "ionic substances" according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are $NH_4$Acetate, $MgCl_2$, $KH_2PO_4$, $Na_2SO_4$, $KCl$, $NaCl$, and $CaCl_2$.

The preferred amino acid is an amino acid with a charged R group (side chain), such as basic amino acids including amino acids selected from arginine, histidine, lysine, etc.

The preferred peptone is a soy peptone, preferably having an average molecular weight of below 1000 g/mol, preferably between 500 and 600 g/mol.

In a preferred embodiment of the invention the ionic substance is added to reach the equilibration balance within protein and cell surface, enough to disrupt the ionic binding and release bound proteins from the cell surface without destroying the cell. According to the invention at least one ionic substance, preferably two and most preferably three or more ionic substances is/are added.

Moreover, it is preferred that no or only small amounts of non-ionic detergents are added to the suspension and/or are present in the release composition. Particularly preferred is that the release composition is free of non-ionic detergents.

The release composition as defined hereinbefore may further comprise a additional buffering substance to stabilize and keep the suspension at a certain pH. It is to be considered that some of the ionic substances defined above do possess excellent buffering properties. Thus, if ionic substances having no or only low buffering properties are utilized, such additional buffering substances are required. The choice of suitable additional buffering substances of course depends on the cell system and the pH to be kept. Such additional buffering substances include HEPES, MES, TRIS, etc. Generally, the pH of the cell suspension when subjected to the increased concentration of the at least one ionic substance is in the range of stability for the selected protein, for FVIII it is about 6.0 to 7.5.

In a preferred embodiment of the invention the ionic substance and its concentration is selected in such a manner that the cells can be continuously cultivated under simultaneous release of the protein. Preferably the protein is then removed from the culture broth using for example a continuous centrifuge or diafiltration over a micro filter membrane. This allows the protection of sensitive proteins from proteolytical degradation, etc., due to fast removal from the culture broth.

In a particularly preferred embodiment the ionic substance and its concentration is selected in such a manner that the viability of the cells is maintained. Also by harvesting of the protein the viability of the cells is maintained, after harvest the non-naturally increased concentration of the ionic substance is reduced or the cells are transferred into fresh culture medium, to enable a cyclic production process of the protein. This enables the claimed process to be run cyclically as set forth in embodiment (3) above.

Furthermore, the preferred mode of addition and the preferred concentration of the preferred ionic substance NaCl, KCl, $CaCl_2$, arginine, histidine and lysine are the following:

NaCl may be added to raise the concentration in the suspension to at least 0.2 M, preferably to a concentration ranging from 0.2 to 2 M, more preferably from 0.4 to 1 M, most preferably to a concentration of about 0.5 M. In particular, the concentration thereof in the suspension may be in the range of 0.2 M up to saturation of the solution, preferably is in the range of 0.2 to 2M, or 0.2 to 1 M, or 0.2 to 0.8 M, or 0.2 to 0.6 M, or 0.2 to 0.5 M, or 0.4 to 1 M, or 0.4 to 0.8 M, or is about 0.5 M.

KCl is added to raise its concentration in the suspension to at least 0.2 M, preferably to a concentration ranging from 0.2 to 2 M, more preferably from 0.4 to 1 M, most preferably to a concentration of about 0.5 M. In particular, the concentration thereof in the suspension may be in the range of 0.2 M up to saturation of the solution, preferably is in the range of 0.2 to 2 M; or 0.2 to 1 M, or 0.2 to 0.8 M, or 0.2 to 0.6 M, or 0.2 to 0.5 M, or 0.4 to 1 M, or 0.4 to 0.8 M, or is about 0.5 M.

$CaCl_2$ may be added to raise its concentration in the suspension to above 0.002 M, preferably >0.002 to 0.5 M, more preferably from 0.05 to 0.2 M, most preferably to a concentration of about 0.1 M. In particular, the concentration thereof in the suspension may be in the range of 0.002M up to saturation of the solution, preferably in the range of 0.002 to 0.5 M, or 0.002 to 0.2 M, or 0.002 to 0.1 M, or 0.002 to 0.05 M, or 0.002 to 0.025 M, or 0.01 to 0.1 M, or 0.05 to 0.15 M, or is about 0.1 M.

Arginine may be added to raise its concentration in the suspension to at least 0.2 M, preferably to a concentration ranging from 0.2 to 2 M, more preferably from 0.4 to 1 M, most preferably to a concentration of about 0.8 M. In particular, the concentration thereof in the suspension is in the range of 0.2 M up to saturation of the solution, preferably may be in the range of 0.2 to 2 M, or 0.4 to 1.5 M, or 0.4 to 1.2 M, or 0.4 to 1.0 M, or 0.4 to 0.8 M, or 0.6 to 0.9 M, or 0.6 to 0.8 M, or is about 0.75 M.

Lysine may be added to raise its concentration in the suspension to at least 0.2 M, preferably to a concentration ranging from 0.2 to 2 M, more preferably from 0.4 to 1 M, most preferably to a concentration of about 0.8 M. In particular, the concentration thereof in the suspension is in the range of 0.2 M up to saturation of the solution, preferably may be in the range of 0.2 to 2 M, or 0.4 to 1.5 M, or 0.4 to 1.2 M, or 0.4 to 1.0 M, or 0.4 to 0.8 M, or 0.6 to 0.9 M, or 0.6 to 0.8 M, or is about 0.75 M.

Histidine may be added to raise its concentration in the suspension to at least 0.01 M, preferably to a concentration ranging from 0.01 to 0.3 M, more preferably from 0.02 to 0.3 M. In particular, the concentration thereof in the suspension is in the range of 0.02 M up to saturation of the solution, preferably may be in the range of 0.02 to 0.3 M, or 0.03 to 0.3 M, or 0.05 to 0.3 M, or 0.1 to 0.3 M, or 0.2 to 0.3 M or is about 0.3 M.

The mixture of peptides and/or amino acids or the peptone is added to raise its concentration in the cell suspension to at least 0.01% (w/w), preferably to a concentration ranging from 0.1 to 20% (w/w) peptone. For a cyclic process it is particularly preferred to use a peptone concentration of 0.2 to 10% (w/w), preferably a peptone concentration of about 5% (w/w). For a non-cyclic (i.e., batch) process it is preferred to use a peptone concentration of 10% (w/w) or greater, preferably a peptone concentration of about 20% (w/w).

In a preferred embodiment of the method of embodiments (1) to (3) as defined above, two ore more ionic substances are mixed with each other, the concentration of each of the added ionic substances is divided with the total amount of added ionic substances, to exert the same releasing capacity as when only one ionic substance is added.

Particularly preferred in the method as defined above is that the ionic substances which are mixed with each other are selected from at least 3 different ionic substances selected from; an amino acid with charged R group (such as arginine, histidine or lysine) in a concentration ranging from 0.05 to 0.2 M; NaCl and KCl in a concentration ranging from 0.1 to 0.2 M and $CaCl_2$ in a concentration ranging from 0.01 to 0.05 M.

The concentration of a mixture of ionic substances needed to reach the desired release of proteins is mainly dependent on two factors, the number of ionic substances and the concentration of each ionic substance. Thus, if more ionic substances are mixed, less concentration of each is needed to reach the maximum product release. In principle, this can be calculated on a mathematical basis. However, in specific cases, the ionic substances can exert combinatorial effects, which lower the need of concentration of ionic substances compared with a theoretical estimation.

If a combination of NaCl and lysine is used in the release composition, the following concentrations are preferably used: NaCl at least 0.1 M, preferably at a concentration ranging from 0.1 to 1 M, more preferably from 0.2 to 0.5 M, most preferably about 0.25 M; lysine at least 0.1 M, preferably at a concentration ranging from 0.1 to 1 M, more preferably from 0.2 to 0.5 M, most preferably about 0.4 M.

If a combination of NaCl, histidine and $CaCl_2$ is used in the release composition, the following concentrations are preferably used: NaCl at least 0.05 M, preferably at a concentration ranging from 0.05 to 0.6 M, more preferably from 0.075 to 0.35 M, most preferably about 0.1 M; histidine at least 0.01 M, preferably at a concentration ranging from 0.01 to 0.3 M, more preferably from 0.025 to 0.15 M, most preferably bout 0.05 M; and $CaCl_2$ at least 0.005 M, preferably at a concentration ranging from 0.01 to 0.25 M, more preferably from 0.025 to 0.15 M, most preferably at about 0.05 M.

It was found that by a combination of ionic substances only a low concentration of each ionic substance is required and therewith the protein releasing properties of the composition is maintained and acceptable cultivation conditions for the cells are provided. In a further preferred embodiment the ionic release composition is selected so that at least one component acts as an stabilizer for the released protein being active before and/or after the separation of protein and cells.

In a further preferred embodiment of the method of embodiments (1) to (3) as defined above the cultivation of the cells may be effected in suspension culture or adherent culture.

Moreover, it is preferred that the separation of the medium from the cultivated cells in steps (b) and (d) is effected by centrifugation, filtration, diafiltration, dead end filtration or micro filtration. A method the skilled artisan may be aware of can be utilized for the isolation of the plasma protein from the medium and its purification. Particularly, this may be effected by using at least one technique selected from immuno-affinity chromatography, affinity chromatography, protein precipitation, buffer exchanges, ionic exchange chromatography, hydrophobic interaction chromatography, mixed mode hydrophobic/ion exchange chromatography media, chelating chromatography, carbohydrate affinity like lectin or heparin affinity chromatography, size-exclusion chromatography, electrophoresis, dialysis, different precipitation agents such as polyethylene glycol, ammonium sulfate, ethanol, hydroxy apatite adsorption, filter membrane adsorption, etc. For a person skilled in the art, it is easily apparent that the carrier (the part on which the active ligand is attached) within the chromatography field, may be comprised of different types of carrier like resins, particles, beads, membranes, hollow fiber, etc., and that the carrier may consist of different materials, like cross linked agarose, cellulose, polysulfon, silica, etc.

In a preferred embodiment of the method of the invention the isolation of the protein comprises a capture step, where the product is bound and cell cultivation media and washing solution is washed away, preferably the capture step utilizes a chromatography media. Furthermore steps (d) and (e) of embodiment (3) may be effected by mixing the cell suspension with a chromatographic medium which binds the product and thereafter the chromatography media is removed from the cell suspension.

It is moreover preferred that the method according to the invention is performed under sterile, in particular good manufacturing practice (GMP) conditions as the resulting product is a pharmaceutical raw material. For the same reason it is preferred that the medium and/or the purified protein is subjected to a virus inactivation step.

According to the invention the cultivation is effected under serum free conditions, which facilitates the work-up of the culture broth and the solution of the plasma protein. In some instances it is preferred to culture under protein-free conditions. Other embodiments, e.g. a process where the ionic substance is a mixture of peptides and/or amino acids (peptone), however, require the addition of functional proteins such as insulin or insulin-like growth factors, etc.

Finally, it is preferred that the cell suspension is processed with a micro filtration system where the pore in the filter has been chosen to retain the cells and the cell suspension thereafter is processed with the release solution through the diafiltration procedure where the concentration of the release solution gradually is increased and the product is recovered in the filtrate of said micro filtration system.

In particular does the invention relate to a method to increase the product recovery during the harvest of FVIII or B-domain deleted FVIII including that defined hereinbefore (hereinafter shortly referred to as FVIII) from cultivated cells. The recovery of FVIII can be significantly increased with relatively simple measures. Due to the addition of ionic substances to the medium prior to the separation of the cells from the cultivation medium,—thereby raising the concentration of those ionic substances above the physiological level found in cells—the FVIII recovery has been increased in the range of 200-2000% (2-20 times).

A suitable explanation seems to be that ionic groups on the cell membrane retard the factor VIII molecules. When the ion-concentration is increased in the medium, which is in contact with the cell surfaces, the ions counteracts the ions on the cell surface, and factor VIII is released.

In a first particularly preferred embodiment of embodiments (1) to (3) of the invention, sodium chloride is increased to 0.5 M NaCl before the removal of the cells from the cultivation media. It was shown that with such release composition the recovery of FVIII in the cell free cultivation media was increased 20 times compared to the use of 0.1 M sodium chloride, whereas the release of host cell proteins was only slightly increased. 0.5 M sodium chloride is not a normal environment for cells (physiological salt conditions is comparable with about 0.15 M sodium chloride), but the treatment did not destroy the cells. However, if the salt concentration is further increased up to 1M sodium chloride, more than 80% of the cells have been destroyed (lysis) and the amount of host cell proteins has almost been doubled, whereas the FVIII concentration is about the same as when using the lower salt concentration (0.5 M).

In a second particularly preferred embodiment of the invention, two or more ionic substances are mixed with each other to achieve the product release. For example, it was shown that if 0.25 M sodium chloride is mixed with 0.25 M of lysine it exerts the same product release properties and cell viability as 0.5 M NaCl. In another example 0.17 M NaCl, 0.17 M lysine and 0.3 M sorbitol was used as release composition. This composition gave slightly lower product release compared with 0.5 M NaCl, but illustrates the huge amount of possibilities to choose and combine ionic release substances with each other, achieving similar product release properties. As also shown, different (non-ionic) stabilizers can be added to the releasing composition, without inhibiting the releasing properties.

In a third particularly preferred embodiment $CaCl_2$ is increased to a range from 0.05 to 0.2 M, preferably 0.1M. It was shown in experimental examples that $CaCl_2$ is superior compared to most of other ionic substances, in regard of product-, host cell protein- and DNA release. In addition, the concentration needed for optimal product release, was significantly lower compared to most of the other ionic substances and this can have a considerably advantages, as an ion-exchange step is often used as capture step for further processing. Thus a lower ionic strength means in many cases less dilution before applying the proteins to the capture step. At the same product recovery, 1-2 times higher values for purity in regard of host cell proteins has been achieved and about 10 fold lower values of DNA, compared with the corresponding NaCl composition (0.55M). It was also shown that the use of $CaCl_2$ in some cases exerted stabilizing effects on the product. This was shown as maintained product activity during stability studies at room temperature during several days and that the ratio between biological activity of the product compared to the FVIII antigen content of the product, was close to one.

In a fourth particularly preferred embodiment of the invention the excellent releasing properties of $CaCl_2$ is combined with that of other releasing substances. For instancey, a release composition comprising 0.05 M $CaCl_2$, 0.05 M histidine and 0.1 M NaCl showed similar releasing properties as compared to 0.1 M $CaCl_2$ alone. This further highlights the possibilities within the invention, to be able to choose an optimal release composition, depending on product and cell characteristics.

The amount and type of impurities obtained during the harvest procedure can be of importance for the further processing and purification of the product. For example, if the amount of proteases is increased, it can contribute to degradation of the product and it might be necessary to add additional purification steps to achieve the very high demand for purity for recombinantly produced products. During experiments, it has been shown that the amount of released host cell proteins and DNA is also dependent on the ionic substance chosen.

With the method of the invention it is possible to achieve the high protein recovery, in particular high FVIII recovery without destroying the cells and thus limiting the amount of impurities coming out together with the product. At present, best results have been achieved with sodium chloride, potassium chloride, calcium chloride, lysine and a combination of sodium chloride and lysine, a combination of calcium chloride and histidine and a combination of calcium chloride sodium chloride and histidine. Especially the use of calcium chloride has shown interesting results, as the concentration needed for release of FVIII is much lower (about 0.1 M) than that of the other substances (about 0.5-0.8 M). This can be very useful, as it has been shown that using calcium chloride releases lower amount of host cell proteins and DNA. Another important embodiment of the invention is the possibility to reuse the cells for further production of proteins, after the salt release procedure has been used. The salt environment is removed and the cells are dissolved in ordinary cultivation media and can continue to produce.

According to embodiment (4) the invention also relates to a protein preparation or pharmaceutical composition obtained by the method of embodiments (1) to (3), in particular to protein preparations and pharmaceutical compositions comprising a blood coagulation factor such as a FVIII or FIX protein. Such preparations possess excellent purity and due to the advantages of the method of the invention. The pharmaceutical compositions comprising a blood coagulation factor such as a FVIII or FIX protein are particularly suitable for the treatment of hemophiliacs. Such compositions may further contain pharmaceutically acceptable carriers, stabilizers, etc. known to the person skilled in the art.

The following examples are given to illustrate the invention. However, these Examples are not to be construed so as to limit the invention.

EXAMPLES

Materials and Methods

Factor VIII: C, Screening Method Based on Coatest:

The method is based on the two-stage principle, and was performed using micro plate technique. In stage one, activated factor X (Xa) is generated via the intrinsic pathway where factor VIII: C acts as a co-factor. In stage two, Factor Xa is then determined by the use of a synthetic chromogenic substrate, S-2222, in the presence of a thrombin inhibitor I-2581 to prevent hydrolysis of the substrate by thrombin. The reaction is stopped with acid, and the VIII:C, which is proportional to the release of pNA (para-nitroaniline), is determined photometrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated. See also literature references (1-4) attached under references.

Total Protein (Protein Determination by Reversed-Phase HPLC):

An HPLC system, equipped with a UV detector and a TSK-gel Octadecyl-NPR column (2.5 µm non-porous particles, 35×4.6 mm I.D., from Tosohaas, Stuttgart, Germany) is used for protein determination. The column, run at 45° C., is equilibrated with 5% acetonitrile in 0.1% trifluoroacetic acid (TFA) (mobile phase A). For elution, 90% acetonitrile in 0.1% TFA (mobile phase B) is used in the linear gradient (0-0.5 min 0% B, 0.5-4 min 0-100% B, 4-5 min 100% B, 5-7 min 0% B). The injection volume is 200 µl and the flow rate is 1.5 ml/min. Detection is carried out by measuring the UV absorbance at 280 nm. Bovine serum albumin (BSA) 10-100 µg/ml (10-20-50-100 µg/ml, n=4) is used for the standard curve. The BSA standard is diluted in 200 mM ammonium acetate and 0.01% Tween® 80, and also the samples, if necessary, is diluted in this solution. The protein concentration in the unknown samples is calculated from the BSA standard curve, which always gives a linear correlation coefficient (r) of >0.99.

Purity (FVIII:C/Total Protein):

The purity for a sample, is calculated taking the value achieved from the FVIII:C analysis and dividing it with the value achieved from the analysis of total protein.

Factor VIII Antigen Analysis (FVIII:Ag):

A microtiter plate is coated with a monoclonal antibody specific for one type of antigenic determinant of the light chain of factor VIII protein in the sample. After incubation with samples a monoclonal peroxidase conjugated antibody is added. This antibody binds to another antigenic determinant of the light chain of factor VIII protein, thus forming a sandwich complex. The enzyme activity, which is proportional to the factor VIII:Ag content in the sample, is then determined through the action of 3,3', 5,5'-Tetramethylbenzidine substrate. The reaction is stopped with acid and the colour is read photometrically at 450 nm against a reagent blank.

Specific Activity (Quotient FVIII:C/FVIII:Ag):

The specific activity of a FVIII sample is calculated taking the value achieved from the FVIII:C analysis and divide it with the value achieved from the analysis of FVIII:Ag. The resulting value shows the relationship between biologically active FVIII and total FVIII protein (including both active and inactive forms). For a fully active protein the quotient, FVIII: c/FVIII:Ag, is 1.

Viability (Living Cells/Dead Cells+Living Cells, %):

Cell suspension is diluted with a 0.4% trypan blue staining solution and the cells are thereafter counted in an inverted phase contrast microscope, thus making it possible to determine the cell concentration. Due to the appearance of the cells, it is also possible to make a distinction between living and dead cells. The viability is calculated by dividing the amount of living cells with the total amount of cells and multiplying the results with 100 to receive the viability percentage value. The viability method is further described in R. I. Freshney, Culture of animal cells, $4^{th}$ ed., p. 183-189, Wiley-Liss (2000).

Western Blot Method 1, FVIII Molecular Mass Distribution:

Proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane, which is subsequently incubated with a blocking agent. Polyclonal sheep antibodies directed to the whole factor VIII molecule is then added followed by a secondary antibody, which is specific for the Fc part of goat/sheep antibodies. As a third step soluble complexes of goat antibody to horseradish peroxidase (HRP) and HRP are added. FVIII polypeptides are then detected by occurrence of blue bands after incubation with the substrate 4-chloro-1-naphtol.

Western Blot Method 2, Sensitivity 0.5 IU/Ml:

Proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane, which is subsequently incubated with a blocking agent. Polyclonal sheep antibody directed to the whole factor VIII molecule is then added followed by a secondary antibody, which is conjugated with horseradish peroxidase and reacts with the heavy and light chains of sheep immunoglobulins. FVIII polypeptides are detected after incubation with the chemiluminescent substrate luminol by exposure to a sensitive X-ray film.

Protease Activity:

Protease activity was determined by a method based on FRET (fluorescence resonance energy transfer) of a fluorescein-casein conjugate. Hydrolysis of casein by proteases release small fluorescein-labeled peptide fragments and an increase in fluorescence is observed. For a quantitative estimate of protease activity, trypsin was used to construct a standard curve. Sample and substrate were incubated on a microplate and the resulting fluorescence was detected with use of a fluorimeter with 485/538 nm excitation/emission wavelengths. The limit of quantification of protease activity corresponded to the proteolytic activity of 500 pg of trypsin/ml when an incubation time of 24 hours was used.

DNA Analysis:

Total DNA is determined using the Treshold Total DNA Assay, which is an enzyme linked assay for single stranded DNA. In the first step the sample is heat denaturated to convert all DNA to the single stranded form. Samples are then incubated with a DNA labeling reagent, which contains conjugates of two binding proteins that have high affinities for DNA independent of base sequence. One conjugate is an anti-DNA monoclonal antibody coupled to urease. The other conjugate is a single stranded DNA binding protein coupled to biotin. After incubation, the labeled DNA complex is transferred to a filtration unit on the work station, where it is captured under vacuum control onto a stick which carries a biotinylated nitrocellulose membrane. An excess of streptavidin in the DNA labeling reagent binds specifically to biotin in the DNA complex, and also to biotin attached to the nitrocellulose membrane of the stick. A subsequent wash removes any non-specifically retained enzyme from the membrane and the stick is then placed in a reader, where it is brought into contact with the sensor surface in a very small volume of fluid which contains the enzyme substrate urea. The enzyme reaction changes the local pH at each measurement site, which changes the surface potential on the sensor. The rate of change in surface potential is proportional to the amount of DNA at each site. The surface potential is monitored kinetically and the samples are then quantitated against a standard curve.

The Product:

The product produced in the cell cultivation is a recombinant form of FVIII that has been genetically engineered to contain the active sites of natural FVIII and to exclude the B-domain dispensable for FVIII activity. It is a full-length 170 KDa FVIII polypeptide of which the major portion is processed to give a heavy chain (HCh, 90 KDa) and a light chain (LCh, 80 KDa) polypeptide. The deletion of the B-domain reduces structural complexity while retaining the biological activity similar to that of plasma-derived FVIII. The amino acid sequence of the FVIII mutein isolated in the following examples is given in SEQ ID NOs:4 and 6.

Example 1

Production of Expression Cell Line

Cell Line:

The expression cell line is based on the cell line HEK 293T (or shortly 293T). This cell line was originally generated by transformation of human foetal kidney cells with sheared adenovirus type 5 DNA (F. L. Graham et al., J. Gen. Virol. 36(1), 59-74 (1974)). Into the resulting cell line HEK 293 (shortly 293) the temperature sensitive gene for SV40 T-antigen was inserted. Features of the expression cell line: Name: HEK 293T tsA201; Source: European Collection of Cell Cultures, ECACC (http://www.ecacc.org.uk/) cell line #9612 1229, tsA 201 (redeposited according to the Budapest Treaty by Octagene Biomedical Laboratories GmbH, Am Klopferspitz 19, 82152 Martinsried, Germany with the DSMZ—Deutsche Sammlung von Mikroorganismen und Zellkulturen GmbH, Maschenroder Weg 1B, 38124 Braunschweig, Germany, on Feb. 3, 2001, under the deposition # DSM ACC 2494; permission to refer to this deposit was granted by Octagene Biomedical Laboratories GmbH on Mar. 17, 2005); Species: Human; Tissue: foetal kidney; Morphology: Epithelial like; Karyotype: The karyotype of 293T cells (ECACC #96121229) is not specified; the karyotype of 293 cells (ECACC #85120602), however, is known and described as 2n=46, hypotriploid, model chromosome number: 64.

Figure 4:
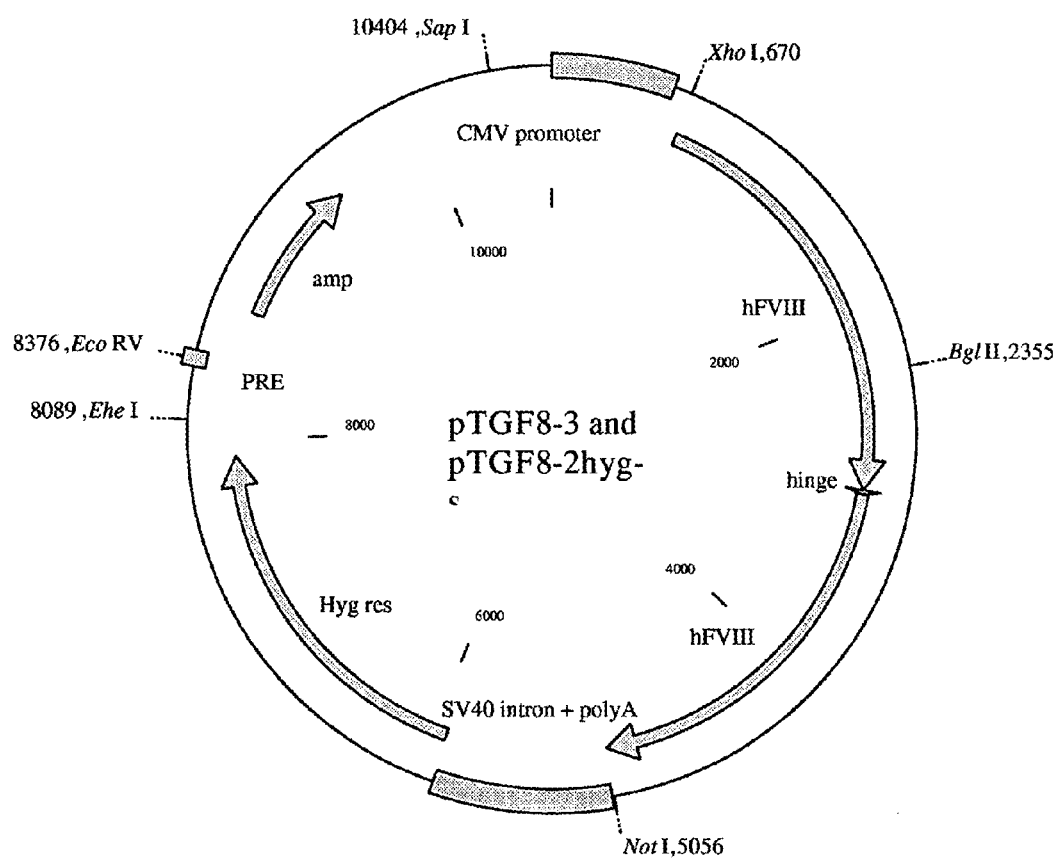
FIG. 4 shows the common molecular structure of pTGF8-3 and pTGF8-2hyg-s, 10698 bps circular DNA, the exact DNA sequences thereof are given in SEQ ID NOs:3 and 5, respectively (for the factor VIII protein encoded by said DNA sequence see SEQ ID NOs:4 and 6, respectively).

Expression Plasmids:

As expression plasmids vectors of the pTGF8 family were used as it can be seen in FIG. 4. The vectors pTGF8-3 and pTGF8-2hyg-s contain the expression cassette for B-domain deleted human clotting factor VIII with the linker peptide of SEQ ID NO:9 (SEQ ID NOs:4 and 6, respectively). pTGF8-2hyg-s further has three amino acid residue exchanges at positions 162, 2011 and 2223 (relative to the full length sequence shown in SEQ ID NO:2). The vectors further contain a cassette for hygromycin resistance (encoding hygromycin-B-phosphotransferase) and a cassette for ampicillin resistance (encoding p-lactamase). Furthermore, a progesterone responsive element (PRE) is contained. The expression of the BDDrFVIII is controlled by a CMV promoter. This promoter in connection with the SV40 intron and the poly-adenylation site provide high level recombinant protein production. The resistance against two antibiotics provides an efficient tool for clone selection after transfection.

Transfection:

Immediately following revitalization of the ECACC stock, adherent 293T cells were transfected with pTGF8-3 or pTGF8-2hyg-s using the calcium phosphate method (C. Chen et al., Mol. Cell. Biol. 7(8), 2745-2752 (1987)). Selection with hygromycin (200 ng/ml) started 72 hours after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clones no. 293T 48/9H5 and 293T 12/24E4.

Adaptation to Serum Free Culture Medium:

Clones no. 293T 48/9H5 and 293T 12/24E4 were adapted to growth in serum-free medium over a period of 6 weeks resulting in non-adherent suspension growing cells. After the adaptation process, the cells where expanded using spinner flasks. From these cells, a pre-MCB was established by freezing them in serum-free cryopreservation medium containing 7.5% DMSO. The cryovials, each containing $1$-$10^7$ cells, were stored in liquid nitrogen. GMP compliant testing of this pre-MCB concerning in-vitro virus assays, mycoplasma- and sterility-testing was carried out.

Cultivation:

Static cultivation of cells was done in TC-flasks of different size. Bottles and 10 l disposable bioreactors were used for dynamic cultivation. For agitation purpose the bottles where placed on a horizontal shaker situated within the incubator. All incubators were set to 5% carbon dioxide, 37° C. and 95% relative humidity.

Cell Suspension:

(Hereinafter shortly referred to as "CS".) As can be seen in the following examples, cell suspension used for different experiments exert different amounts of FVIII and host cell proteins. This reflects that the initial material has been taken out at different times in the production cycle (see FIG. 1) and thus some CS have faced more optimal production conditions than others.

Example 2

FVIII Release Using Different Concentration of NaCl and Lysine as Releasing Substances 5 ml of CS1 ($1.6 \times 10^6$ cells/ml, clone HEK 293T 48/9H5, vector pTGF8-3)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analyzed for FVIII:C, etc. For a general schematic description of the experiment, see also FIG. 2. The release composition added and the corresponding results are shown in Tables 1 and 2, respectively.

TABLE 1

| Release component | Buffer substances |
| --- | --- |
| Reference (CS1) | No addition |
| 0.10M NaCl | 20 mM MES, 10 mM CaCl2, 0.01% Tween ® 80, pH 6.5 |
| 0.50M NaCl | 20 mM Histidine, pH 6.0 |
| 1.0M NaCl | 20 mM Histidine, pH 6.0 |
| 2.0M NaCl | 20 mM Histidine, pH 6.0 |
| 1.0M Lysine | 0.10M NaCl, 20 mM MES, 10 mM $CaCl_2$, 0.01% Tween ® 80, pH 7.5 |

TABLE 2

| Release conc.* | FVIII:C, (IU/ml) | Recovery (%) | FVIII:C × $10^{-6}$/ cell (IU) | Proteases** (a.u.) |
| --- | --- | --- | --- | --- |
| Reference | 1.7 | 100 | 1.2 | <1 |
| 0.10M NaCl | 7.0 | 412 | 4.6 | <1 |
| 0.30M NaCl | 8.0 | 470 | 5.4 | 14 |
| 0.55M NaCl | 33.2 | 1953 | 22.2 | 19 |

TABLE 2-continued

| Release conc.* | FVIII:C, (IU/ml) | Recovery (%) | FVIII:C × $10^{-6}$/ cell (IU) | Proteases** (a.u.) |
| --- | --- | --- | --- | --- |
| 1.0M NaCl | 36.4 | 2141 | 24.2 | 19 |
| 0.50M lysine | 31.8 | 1871 | 21.2 | <1 |

*The final release concentration is half of the added release solution due to the mixing with the CS. The conductivity in the CS is calculated to correspond to about 0.1M NaCl.
**Definition of protease activity: 1 arbitrary unit (a.u.) of protease activity is defined as the activity corresponding to the activity of 1 μg of trypsin/l.

Conclusion:
Increase of sodium chloride or lysine concentration before the harvest significant increase the recovered FVIII.

Example 3

5 ml of CS2 ($2.84 \times 10^6$ cells/ml, clone HEK 293T 12/24E4, vector pTGF8-2hyg-s)) was added to 5 ml of a releasing solution. The cells had been cultivated as described in Example 1 and were withdrawn before harvest (see FIG. 1). The suspension was gently mixed (using a wave mixer) for 1 h at room temperature (21° C.) using 15 ml tubes. The tubes were then centrifuged at 1200×g for 1 minute to remove the cells, where after the cell supernatant was analyzed (FVIII:C, FVIII:Ag, cell viability and total protein). For a schematic description of the experiment, see also FIG. 2. Examples 3A-3C are experiments performed with the same cell suspension in parallel experiments and are thus directly comparable to each other.

Example 3A

Release with Different Concentration of Sodium Chloride

Different concentrations of NaCl were prepared and added to CS2 according to the above-described procedure, to study in which range of sodium chloride concentration the release of FVIII occurs. The results are summarized in Table 3.

TABLE 3

| Release conc.* | FVIII:C (IU/ml)** | FVIII:C (%) | FVIII:C × $10^{-6}$/ cell (IU) | Cell Viability (%) | Purity FVIII (IU/μg prot.) | ratio FVIII:C/ FVIII:ag |
| --- | --- | --- | --- | --- | --- | --- |
| Ref. (CS2) | 0.50 | 100 | 0.36 | 36 | 3.4 | 0.57 |
| 0.10M NaCl | 1.42 | 248 | 0.90 | 40 | 4.6 | NA |
| 0.15M NaCl | 1.28 | 256 | 0.94 | 44 | 5.2 | NA |
| 0.25M NaCl | 2.00 | 400 | 1.46 | 50 | 7.7 | NA |
| 0.45M NaCl | 3.56 | 712 | 5.20 | 48 | 26.6 | NA |
| 0.55M NaCl | 4.16 | 832 | 6.08 | 36 | 28.1 | 0.62 |
| 1.0M NaCl | 4.28 | 856 | 6.28 | 8 | 17.8 | 0.50 |
| 2.0M NaCl | 4.42 | 884 | 6.46 | 3 | 15.7 | 0.60 |

*The final wash concentration and the conductivity in the CS are calculated to correspond to about 0.1M NaCl.
**FVIII:C concentration compensated for dilution factors.
NA: not analysed.

Conclusion:
Increased sodium chloride concentration increases the FVIII:C and a plateau is reached at 0.55 M NaCl. The release of FVIII is to a smaller degree achieved by a dilution effect (CS compared with 0.1 M NaCl in table 3). The cell membrane is destroyed if the sodium chloride concentration is increased too much (1.05 M and 2.00 M), whereas the cell viability seems to be approximately unchanged in the interval of 0.1-0.55 M NaCl. The purity of released FVIII reaches a maximum in the 0.45 and 0.55 M NaCl samples, whereas it decreases at the higher salt concentrations due to the release of intracellular host cell proteins caused by cell membrane destruction and/or release of proteins located on the membrane/membrane fragments. Thus, an optimal choice of conditions is to use the highest sodium chloride concentration, which does not destroy the cell membrane. The quotient FVIII:C/FVIII:ag indicates an unchanged biological activity of the released FVIII molecules. The results indicate that the main part of FVIII that is released during the increase of the sodium chloride concentration, mainly is located outside the cell, bound through ionic interactions on the cell surface. This is based on the fact that FVIII recovery does not significantly increase when the cell membrane is disrupted.

Example 3B

Study of Different pH within Different NaCl Concentrations

The pH was adjusted in the range of 6.0-7.5 (pH range in which FVIII is known to be stable) both in the CS2 (0.1 M NaCl) and in the CS2 diluted with the wash substance (final concentration 0.55 M NaCl). To study how different pH affects the release of FVIII. The results are summarized in Table 4.

TABLE 4

| Release concentration* | pH | FVIII:C (IU/ml)** | FVIII:C (%) |
| --- | --- | --- | --- |
| CS2 (0.10M NaCl) | 6.0 | 0.46 | 92 |
| CS2 (0.10M NaCl) | 6.5 | 0.50 | 100 |
| CS2 (0.10M NaCl) | 7.2 | 0.50 | 100 |
| CS2 (0.10M NaCl) | 7.5 | 0.53 | 106 |
| 0.55M NaCl | 6.0 | 4.10 | 820 |
| 0.55M NaCl | 6.5 | 4.34 | 868 |
| 0.55M NaCl | 7.0 | 4.30 | 860 |
| 0.55M NaCl | 7.5 | 3.56 | 712 |

*The conductivity in the CS is calculated to correspond to about 0.1M NaCl.
**FVIII:C concentration compensated for dilution factor.

Conclusion:

The pH has no significant effect of the release of FVIII within the pH interval tested (which was selected due to the pH stability of the FVIII molecule). The major difference in FVIII recovery between high (0.55 M NaCl) and low (0.1 M NaCl) of release concentration is independent of pH. The FVIII pH stability (pH 6-7) is discussed at p. 10 of Wang et al., International Journal of Pharmaceutics 259, 1-15 (2003).

Example 3C

Different Concentration of Lysine as a Release Component

Different concentrations of lysine was prepared and added to CS2 according to the above described procedure, to study in which range of lysine concentration the release of FVIII occurs. The results are summarized in Table 5.

TABLE 5

| Release conc.* | FVIII:C, (IU/ml)** | FVIII:C (%) | FVIII:C × $10^{-6}$/ cell (IU) | Cell Viability (%) | Purity FVIII (IU/μg prot.) | Ratio FVIII:C/ FVIII:ag |
| --- | --- | --- | --- | --- | --- | --- |
| Ref. (CS2) | 0.50 | 100 | 0.36 | 36 | 3.4 | 0.57 |
| 0.15M lysine | 0.82 | 164 | 0.58 | 33 | 5.9 | 0.53 |
| 0.30M lysine | 1.37 | 274 | 0.96 | 40 | 9.4 | 0.39 |
| 0.5M lysine | 2.88 | 576 | 2.03 | 19 | 16.7 | 0.42 |

*The final release concentration, the conductivity in the CS is calculated to correspond to about 0.1M NaCl.
**FVIII:C concentration compensated for dilution factor.

Conclusion:

Lysine, a charged amino acid, releases FVIII. However, sodium chloride (Example 3A) seems to be a more effective and lenient releaser of FVIII, when compared at similar concentrations. It seems that the cells are more damaged by lysine than sodium chloride, as can be seen when comparing viability, purity and quotient FVIII:C/FVIII:ag.

Example 4

Study of Kinetic and Different Releasing Substances 5 ml of CS3 ($1.6 \times 10^6$ cells/ml, clone HEK 293T 48/9H5, vector pTGF8-3)) was added to 5 ml of a releasing solution. The cells had been cultivated as described in Example 1 and were withdrawn during the growth phase (C in FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C, etc. For a general schematic description of the experiment, see also FIG. 2. Examples 4A-4E are experiments performed with the same CS in parallel experiments and are thus directly comparable to each other.

Example 4A

Study of Time Needed for Release of FVIII using 0.55 M NaCl

A release solution of 0.10 M and 1.0 M of sodium chloride was prepared and added to CS3 according to the above-described procedure. Samples were withdrawn after 0, 5, 10, 20, 40 and 60 minutes to study how fast FVIII was released. The results are summarized in Table 6.

TABLE 6

| Release concentration* | Time (minutes) | FVIII:C,** (IU/ml) | FVIII:C (%) | FVIII:C × $10^{-6}$/cell (IU) |
| --- | --- | --- | --- | --- |
| 0.10M NaCl | 60 | 0.12 | 100 | 0.08 |
| 0.55M NaCl | 0 | 1.26 | 1050 | 0.79 |
| 0.55M NaCl | 5 | 1.30 | 1083 | 0.81 |
| 0.55M NaCl | 10 | 1.36 | 1133 | 0.85 |
| 0.55M NaCl | 20 | 1.26 | 1050 | 0.79 |
| 0.55M NaCl | 40 | 1.34 | 1117 | 0.84 |
| 0.55M NaCl | 60 | 1.26 | 1050 | 0.79 |

*The final release concentration, the conductivity of the CS is calculated to correspond to about 0.1M NaCl.
**FVIII:C concentration compensated for dilution factors.

Conclusion:

The increased salt concentration releases the FVIII molecules instantly. The incubation time has no effect on the recovery. This is an important finding that broadens the possible use of the invention, making it possible to use different techniques (dead end filtration, tangential filtration, centrifugation, etc.) to separate the FVIII molecule from the cell using the release procedure. A very interesting approach would be to add—during a perfusion batch (perfusion means normally a slowly continuously harvested cell suspension, where the cells can be used for months to produce the product)—the release buffer with increased ionic concentration, remove the release buffer and thereafter add the cultivation buffer and continue to use the cells to produce FVIII. Due to this procedure, the productivity of the cells can significantly be increased, compared to the normal procedure where either the cells are discarded (destroyed) after the harvest (it takes 1-2 weeks to cultivate new cells up to desired cell concentration) or use the normal slow perfusion harvest with low ionic content and the lower recovery.

Example 4B

Study of Release Composition Using Different NaCl Concentration

Different concentrations of NaCl were prepared and added to CS3 according to the above-described procedure, to study in which range of sodium chloride concentration the release of FVIII occurs. The results are summarized in Table 7 (see also example 3A for a similar NaCl study with another CS and additional analyses performed).

TABLE 7

| Release concentration* | FVIII:C** (IU/ml) | FVIII:C (%) | FVIII:C × $10^{-6}$/cell (IU) | Viability (%) |
|---|---|---|---|---|
| 0.10M NaCl | 0.12 | 100 | 0.08 | 89 |
| 0.30M NaCl | 0.76 | 633 | 0.48 | 92 |
| 0.40M NaCl | 1.03 | 858 | 0.64 | 93 |
| 0.50M NaCl | 0.98 | 817 | 0.61 | 90 |
| 0.55M NaCl | 1.26 | 1050 | 0.79 | NA |
| 0.60M NaCl | 1.10 | 917 | 0.69 | 88 |

*The final release concentration, the conductivity in the CS is calculated to correspond to about 0.1M NaCl.
**FVIII:C concentration compensated for dilution factors.
NA: not analysed.

Conclusion:

The FVIII release starts at about 0.30 M NaCl and reaches a peak at about 0.55 M NaCl. There is no significant difference in cell viability, within the NaCl concentration tested.

Example 4C

Study of Lysine as a Release Substance Compared with NaCl

Different concentrations of lysine was prepared (pH was adjusted to 7.0) and added to CS3 according to the above described procedure, to study at which level the maximum release of FVIII occurred compared with sodium chloride as releasing substance. The results are summarized in Table 8.

TABLE 8

| Wash concentration* | FVIII:C,** (IU/ml) | FVIII:C (%) | FVIII:C × $10^{-6}$/cell (IU) |
|---|---|---|---|
| 0.10M NaCl | 0.12 | 100 | 0.08 |
| 0.55M NaCl | 1.26 | 1050 | 0.79 |
| 0.50M lysine | 1.08 | 900 | 0.68 |

TABLE 8-continued

| Wash concentration* | FVIII:C,** (IU/ml) | FVIII:C (%) | FVIII:C × $10^{-6}$/cell (IU) |
|---|---|---|---|
| 0.75M lysine | 1.24 | 1033 | 0.78 |
| 1.0M lysine | 1.22 | 1017 | 0.76 |

*The final release concentration, the conductivity of the CS is calculated to correspond to about 0.1M NaCl.
**FVIII:C concentration compensated for dilution factors Conclusion:

Lysine can be used as a release substance with the same degree of total FVIII release compared with sodium chloride. It seems that sodium chloride is a little bit more effective to release FVIII in regard of concentration (M) needed to achieve the same recovery.

Example 4D

Study of Different Types of Potential Release Compositions

Different buffers was prepared (pH was adjusted to 7.0 if applicable) and added to CS3 according to the above described procedure, to study if release of FVIII occurred. The results are summarized in Table 9.

TABLE 9

| Buffer concentration* | FVIII:C,** (IU/ml) | FVIII:C (%) | FVIII:C × $10^{-6}$/cell (IU) | Viability (%) |
|---|---|---|---|---|
| 0.10M NaCl | 0.12 | 100 | 0.08 | NA |
| 0.55M NaCl | 1.26 | 1050 | 0.79 | NA |
| 0.50M lysine | 1.08 | 900 | 0.68 | NA |
| 0.50M arginine | 0.48 | 400 | 0.30 | NA |
| 0.25M histidine | 0.54 | 450 | 0.34 | NA |
| 0.50M glycine | <0.1 | <90 | <0.08 | NA |
| 0.50M KCl | 1.64 | 1367 | 1.02 | NA |
| 0.50M ammonium acetate | 0.92 | 767 | 0.58 | NA |
| 0.50M $MgCl_2$ | 1.30 | 1083 | 0.81 | NA |
| 0.50M sorbitol | <0.1 | <90 | <0.08 | 90 |
| 1% Triton ® X-100 | 0.86 | 716 | 0.54 | 0 |

*The conductivity in the CS is calculated to correspond to about 0.1M NaCl.
**FVIII:C concentration compensated for dilution factors.
NA: not analysed.

Conclusion:

As already has been shown in previous examples, sodium chloride and lysine can be used as release substances with about the same degree of FVIII release. As shown in this example a lot of charged substances can achieve similar effects but not all, to the same level. When some charged amino acids was compared with each other, lysine was a more effective releasing agent of FVIII compared with arginine and histidine (however due to low solubility histidine concentration could only be raised to 0.25 M). A very interesting observation was that an amino acid with uncharged R-group (glycine) and a sugar (sorbitol) did not release FVIII at all. This gives a clear indication that the main force that retains the FVIII molecule is of ionic origin. The detergent, 1% Triton® x-100, which is known in the prior art to disrupt the cell membrane and release all proteins that have been inside the cells, was included in the experiment to study to which degree FVIII was trapped inside the cell. When studying the cells before and after the treatment with detergent, no cells or traces of cells could be seen after the detergent treatment, thus all cell material has been dissolved. The FVIII concentration in the sample, which had been detergent treated, was in principle the same as for the highest 0.50 M values (with the main part of the cells intact after treatment). This indicates that when using the releasing procedure, the main part of the released FVIII is originating from binding to cells surfaces outside the cell, this theory is also strengthen by the instant release of FVIII when using the washing procedure (example 4A).

Example 4E

Study of Combination of Releasing Substances

Different buffers were prepared in which different release substances were mixed (pH was adjusted to 7.0 if applicable) and added to CS3 according to the above described procedure, to study if the recovery of FVIII was changed compared to when using only one realeasing substance. The results are summarized in Table 10.

TABLE 10

| Release concentration* | FVIII:C,** (IU/ml) | FVIII:C (%) | FVIII:C × $10^{-6}$/ cel (IU) | Viabilty (%) |
|---|---|---|---|---|
| 0.10M NaCl | 0.12 | 100 | 0.08 | 89 |
| 0.30M NaCl | 0.76 | 633 | 0.48 | 92 |
| 0.60M NaCl | 1.26 | 1050 | 0.79 | 88 |
| 0.50M lysine | 1.08 | 900 | 0.68 | NA |
| 1% Triton ® X-100 | 0.86 | 716 | 0.54 | 0 |
| 0.60M NaCl + 1% Triton ® | 0.92 | 766 | 0.57 | 0 |
| 0.25M NaCl + 0.25M lysine | 1.12 | 933 | 0.70 | NA |

TABLE 10-continued

| Release concentration* | FVIII:C,** (IU/ml) | FVIII:C (%) | FVIII:C × $10^{-6}$/ cel (IU) | Viabilty (%) |
|---|---|---|---|---|
| 0.17M NaCl + 0.17M lysine + 0.33M sorbitol | 0.94 | 783 | 0.59 | NA |

*The conductivity in the CS is calculated to correspond to about 0.1M NaCl.
**FVIII:C concentration compensated for dilution factors.
NA: not analysed.

Conclusion:

Different release substances can be combined to release the FVIII molecule.

Example 5

Study of Different Charged Substances as Releasing Agent 5 ml of CS4 (6.37×$10^6$ cells/ml, clone HEK 293T 48/9H5, vector pTGF8-3)) was added to 5 ml of a releasing solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C, etc. For a general schematic description of the experiment, see also FIG. 2. Examples 5A-5D are experiments performed with the same CS batch in parallel experiments and are thus directly comparable to each other.

Example 5A

Study of Different Concentrations of KCl as Release Composition and Compared with NaCl Different concentrations of KCl were prepared and added to CS4 according to the above described procedure, to study in which range of sodium chloride concentration the release of FVIII occurs and to compare it with NaCl. The results are summarized in Table 11.

TABLE 11

| Release conc.* | FVIII:C, (IU/ml) | FVIII:C (%) | FVIII:C × $10^{-6}$/ cell (IU) | Cell Viability (%) | Purity FVIII, IU/μg prot. | Proteases** (a.u) |
|---|---|---|---|---|---|---|
| 0.10M KCl | 0.26 | 100 | 0.08 | 87 | NA | 82 |
| 0.15M KCl | 0.64 | 260 | 0.20 | 85 | NA | NA |
| 0.20M KCl | 1.21 | 480 | 0.38 | 86 | NA | NA |
| 0.25M KCl | 2.30 | 920 | 0.72 | 82 | NA | NA |
| 0.38M KCl | 4.47 | 1790 | 1.40 | 64 | NA | NA |
| 0.50M KCl | 4.42 | 1770 | 1.39 | 70 | 0.32 | 60 |
| 1.0M KCl | 5.08 | 2030 | 1.60 | 30 | 0.13 | 92 |
| 0.10M NaCl | 0.25 | 96 | 0.08 | 85 | 0.03 | 82 |
| 0.55M NaCl | 4.96 | 1980 | 1.56 | 80 | 0.35 | 73 |

*The final release concentration, the conductivity in the CS is calculated to correspond to about 0.1M NaCl.
NA: not analysed.
**Definition of protease activity: 1 arbitary unit of protease activity is defined as the activity corresponding to the activity of 1 μg of trypsin/l.

Conclusion:

The ability for different KCl concentrations to release FVIII is comparable with NaCl. Also the cell viability, purity and protease release are almost the same compared with those of NaCl. However, there is a small trend that may be NaCl is milder against the cells, when comparing the cell viability and the purity within similar concentrations. A decreased purity is an indication of cell damage as can be seen for the 1 M KCl wash solution, in which the purity has significantly decreased, indicating in combination with the decreased cell viability, that host cell proteins have been released due to lysis of the cell membrane.

Example 5B

Study of Different Charged Release Compositions

Different release compositions were prepared (pH was adjusted to 7.0 if applicable) and added to CS4 according to the above described procedure, to study if release of FVIII occurred. The results are summarized in Table 12.

TABLE 12

| Release conc.* | FVIII:C, (IU/ml) | FVIII:C (%) | FVIII:C × $10^{-6}$/ cell (IU) | Cell Viability (%) | Purity FVIII, IU/µg prot. | Proteases*** (a.u) |
|---|---|---|---|---|---|---|
| 0.10M NaCl | 0.25 | 100 | 0.08 | 85 | 0.03 | 82 |
| 0.55M NaCl | 4.96 | 1980 | 1.56 | 80 | 0.35 | 73 |
| 0.50M KCl | 4.42 | 1768 | 1.39 | 70 | 0.32 | 60 |
| 0.50M $Na_2SO_4$ | 3.21 | 1284 | 1.01 | 34 | NA | 109 |
| 0.50M $KH_2PO_4$ | 3.62 | 1448 | 1.14 | 44 | NA | 94 |
| 0.25M $CaCl_2$ | 5.34 | 2136 | 1.68 | 78** | 0.53 | NA |
| 0.50M $MgCl_2$ | 2.26 | 904 | 0.71 | 16** | NA | NA |
| 0.75M lysine | 6.10 | 2440 | 1.92 | 75 | 0.20 | 113 |

*The final release concentration, the conductivity in the CS is calculated to correspond to about 0.1M NaCl.
**Difficulties within analysis as washing substance was precipitated when analytical chemical was added, during measurement.
***Definition of protease activity: 1 arbitary unit of protease activity is defined as the activity corresponding to the activity of 1 ug of trypsin/L.
NA: not analysed.

Conclusion:

Different charged substances can be used to release FVIII (as also shown in example 3D). However, as shown in some of the previous examples, it is preferable to choose a release substance which not destroys the cell membrane, as this releases host cell proteins and proteases which decrease the purity and can decrease the stability of the of the product. In addition, if the cells are destroyed, they cannot be used for continuous production of the product, which decrease the overall yield. It can be noted that 0.55 M NaCl, 0.50 M KCl and 0.25 M $CaCl_2$ all gives a very high recovery with almost unchanged cell viability and with a high purity of released product.

Example 6

Study of Calcium Chloride as Release Composition and Comparison with NaCl 5 ml of a CS5 ($3.47 \times 10^{-6}$ cells/ml, clone HEK 293T 48/9H5, vector pTGF8-3)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII: C, etc. For a general schematic description of the experiment, see also FIG. 2. Examples 6A-6E are experiments performed with the same CS batch in parallel experiments and are thus directly comparable to each other.

A:

Study of different concentrations of $CaCl_2$ as release composition and compared with NaCl.

Different concentrations of $CaCl_2$ were prepared and added to CS5 according to the above-described procedure, to study in which range of calcium chloride concentration the release of FVIII occurs. The results are summarized in Table 13.

TABLE 13

| Release concentration* | FVIII:C, (IU/ml) | FVIII:C (%) | FVIII:C × $10^{-6}$/ cell (IU) | Cell Viability (%) | Purity FVIII, IU/ µg prot. |
|---|---|---|---|---|---|
| 0.10M NaCl | 5.06 | 100 | 2.92 | 94 | 0.22 |
| 0.55M NaCl | 13.6 | 269 | 7.86 | 82 | 1.05 |

TABLE 13-continued

| Release concentration* | FVIII:C, (IU/ml) | FVIII:C (%) | FVIII:C × $10^{-6}$/ cell (IU) | Cell Viability (%) | Purity FVIII, IU/ µg prot. |
|---|---|---|---|---|---|
| 0.05M $CaCl_2$ | 15.1 | 298 | 8.73 | 71** | 2.16 |
| 0.10M $CaCl_2$ | 18.0 | 356 | 10.4 | 77** | 1.80 |
| 0.20M $CaCl_2$ | 7.32 | 145 | 4.23 | 52** | 0.46 |

*The final release concentration, the conductivity in the CS is calculated to correspond to about 0.1M NaCl.
**uncertain results as $CaCl_2$ precipitates during the adding of analytical reagents.

Figure 3:
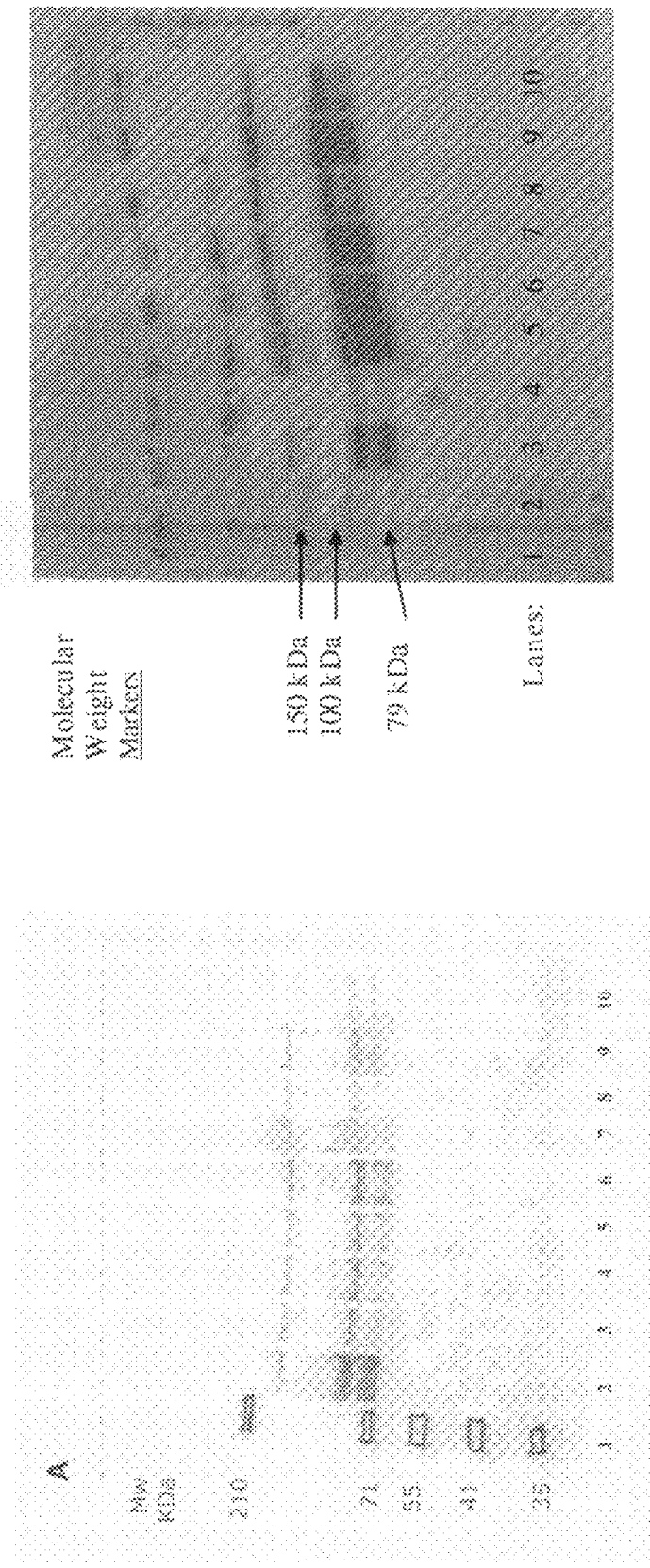
FIG. 3 shows Western Blot analysis of crude research material harvested with different release compositions (FIG. 3A lanes 3 to 6, FIG. 3B lanes 2 to 8) which is compared with molecular markers (FIGS. 3A and 3B lane 1, respectively) and high purified FVIII product FIG. 3A lane 2).

Conclusion:

Calcium chloride can be used as an effective releaser of FVIII in the cell harvest procedure. A 10 fold lower concentration of calcium chloride (0.05 M) has the same releasing effect as compared to the higher sodium chloride concentration (0.55 M). In additional the calcium chloride wash seems to release significant lower amounts of other host cell proteins, resulting in that the purity of released FVIII significantly increased compared to that of using sodium chloride. The cell viability of the cells treated with calcium chloride seems to be slightly lower compared to the sodium chloride wash, this is however uncertain because of influence of Ca to the viability measurement method. Cell aggregation and not lysis of the cells, is a possible explanation strengthen by the still low amount of host cells proteins released (it is known that calcium chloride can induce aggregation within cells). The western blot analysis indicates that there is no significant difference in molecular mass pattern of the crude FVIII, released with 0.10M NaCl, 0.55M NaCl, 0.10 M $CaCl_2$ and 0.20M $CaCl_2$ (FIGS. 3A and 3B) and compared with a highly purified FVIII preparation (FIG. 3A).

B:

Study of cell cultivation media added with different amounts of $CaCl_2$ as release composition.

Unused cell cultivation medium (the same as used during cell cultivation, Freestyle) was used as buffer solution. The cell cultivation media (CCM) was added to different amounts of $CaCl_2$, in order to study the FVIII release. The results are summarized in Table 14.

TABLE 14

| Release composition* | FVIII:C, (IU/ml) | FVIII:C (%) | FVIII:C × $10^6$/cell (IU) | Cell Viability (%) |
|---|---|---|---|---|
| Reference, 0.10M NaCl | 5.06 | 100 | 2.92 | 94 |
| CC M + 0.005M CaCl$_2$ | 9.72 | 192% | 5.60 | 91% |
| CC M + 0.01M CaCl$_2$ | 9.12 | 180% | 5.26 | 70% |

*The final release concentration, the conductivity in the CS is calculated to correspond to about 0.1M NaCl.

Conclusion:

A small increase (5-10 mM) in the calcium chloride concentration in the CCM, significantly increases the FVIII release.

Example 7

Study of Different Substances of Non-Charged Origin and Compared with NaCl as Release Composition 5 ml of a CS6 (2.96×10$^6$ cells/ml, clone HEK 293T 12/24E4, vector pTGF8-2hyg-s)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C activity, etc. For a general schematic description of the experiment, see also FIG. 2. Examples 7A-7B are experiments performed with the same CS batch in parallel experiments and are thus directly comparable to each other.

A:

Study of different (uncharged) substances and compared with NaCl as release composition. Different solutions were prepared and added to CS6 according to the above-described procedure, to study if FVIII release occurs with substances working with different principles (non-ionic). The results are summarized in Table 15.

TABLE 15

| Release composition* | FVIII:C (IU/ml) | FVIII:C (%) | FVIII:C × $10^{-6}$/cell (IU) | Cell Viability (%) |
|---|---|---|---|---|
| 0.10M NaCl | 0.21 | 100 | 0.14 | 59 |
| 0.55M NaCl | 0.96 | 457 | 0.65 | 54 |
| 10% polyethylene glycol 4000 | 0.12 | 57 | 0.08 | 75 |
| 5% ethylene glycol | 0.20 | 95 | 0.14 | 50 |
| 10% ethylene glycol | <0.1 | <50 | <0.07 | 26 |
| 0.5M alanine | 0.18 | 86 | 0.12 | 62 |
| 0.25M valine | 0.25 | 119 | 0.17 | 68 |
| 10% ethanol | 0.11 | 52 | 0.07 | 32 |
| 5% sodium caprylate | <0.1 | <50 | <0.07 | Na |

*The final release concentration, the conductivity in the CS is calculated to correspond to about 0.1M NaCl.

Conclusion:

Different substances of non-ionic origin (hydrophilic, hydrophobic, alcohols) have been tested and the results have been compared with sodium chloride as release substance. The result shows that release substances of ionic nature are needed for the release of FVIII.

B:

0.55 M NaCl as release substance, concentration and analysis with western blot. 50 ml of CS6 was added to 50 ml of a 1 M NaCl solution. The mixture was gently rocked for 1 hour in room temperature, where after the solution was centrifuged 5 minutes (1200×g) and the supernatant was recovered. The cell supernatant was there after concentrated to a FVIII:C content of 13.6 IU/ml, using centrifugation containers including a 10 kDa membrane (Amicon, centriprep). The centrifugation was necessary to be able to use the Western blot analytical method 1 as a tool, to increase the FVIII concentration.

Conclusion:

The molecular mass distribution of the crude FVIII released with 0.55M NaCl and compared with a highly purified commercially available FVIII preparation, shows a similar molecular mass distribution (FIG. 3A).

Example 8

Study of Different Concentrations of CaCl$_2$ as a Release Substance and Comparison with High (0.55 M) and low (0.1 M) NaCl

A:

5 ml of CS7 (3.41×10$^6$ cells/ml, clone HEK 293T 48/9H5, vector pTGF8-3)) was added to 5 ml of a release composition. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C activity, etc. For a general schematic description of the experiment, see also FIG. 2.

Different concentrations of CaCl$_2$ were prepared and added to CS7 according to the above-described procedure, to study in which range of CaCl$_2$ concentration the release of FVIII occurs. The results are summarized in Table 16.

TABLE 16

| Release concentration* | FVIII:C, (IU/ml) | FVIII:C (%) | FVIII:C × $10^{-6}$/cell (IU) | Cell Viability (%) |
|---|---|---|---|---|
| 0.10M NaCl | 3.65 | 100 | 2.14 | 90 |
| 0.075M CaCl$_2$ | 9.42 | 258 | 5.52 | 73** |
| 0.10M CaCl$_2$ | 10.5 | 288 | 6.16 | 69** |
| 0.125M CaCl$_2$ | 11.7 | 320 | 6.86 | 67** |

*The final wash concentration, the conductivity in the CS is calculated to correspond to about 0.1M NaCl.
**uncertain results as CaCl$_2$ precipitates during the adding of analytical reagents.

Conclusion:

CaCl$_2$ is a release substance, which release FVIII at relatively low concentration. The concentration needed is significant lower compared with NaCl.

B:

Study of time needed for release of FVIII using 0.1 M CaCl$_2$. A release solution of 0.10 M CaCl$_2$ was prepared and added to the cell suspension according to the above described procedure. Samples were withdrawn after 0, 10, 30 and 60 minutes to study how fast FVIII was released. The results are summarized in Table 17.

TABLE 17

| Release concentration* | Time, (minutes) | FVIII:C, (IU/ml) | FVIII:C × $10^{-6}$/cell (IU) |
|---|---|---|---|
| Reference, CS7 | 0 | 3.65 | 2.14 |
| 0.10M CaCl$_2$ | 0 | 9.34 | 5.48 |

TABLE 17-continued

| Release concentration* | Time, (minutes) | FVIII:C, (IU/ml) | FVIII:C × $10^{-6}$/ cell (IU) |
|---|---|---|---|
| 0.10M $CaCl_2$ | 10 | 10.7 | 6.28 |
| 0.10M $CaCl_2$ | 30 | 10.3 | 6.04 |
| 0.10M $CaCl_2$ | 60 | 10.5 | 6.16 |

*The final release concentration, the conductivity in the CS is calculated to correspond to about 0.1M NaCl.

Conclusion:

The release of FVIII using 0.1 M $CaCl_2$ occurs fast, within minutes the main part of FVIII has been released.

Example 9

Study of Different Concentrations of $CaCl_2$ as Release Composition and Comparison with NaCl 5 ml of a CS8 ($3.1 \times 10^4$ cells/ml, clone HEK 293T 12/24E4, vector pTGF8-2hyg-s) was added to 5 ml of release composition. The cells had been cultivated as described in Example 1. The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C. For a general schematic description of the experiment, see also FIG. 2. Different concentrations of $CaCl_2$ was prepared and added to the cell suspension according to the above-described procedure to study in which range of calcium chloride concentration the release of FVIII occurs. The results are summarized in Table 18.

TABLE 18

| Release conc.* | FVIII:C (IU/ml) | FVIII:C (%) | FVIII:C × $10^{-6}$/ cell (IU) | Ratio FVIII:C/ FVIII:Ag | Purity FVIII:C/protein, (IU/ug) | DNA/FVIII (ug/IU) |
|---|---|---|---|---|---|---|
| 0.1M NaCl | 1.48 | 100 | 0.48 | 0.63 | 0.026 | 0.69 |
| 0.55M NaCl | 10.2 | 689 | 3.29 | 0.72 | 0.160 | 0.91 |
| 0.01M $CaCl_2$ | 1.14 | 77 | 0.37 | 0.51 | 0.020 | NA |
| 0.01M $CaCl_2$ + 0.10M NaCl | 2.12 | 143 | 0.68 | 0.56 | 0.050 | NA |
| 0.04M $CaCl_2$ | 3.32 | 224 | 1.07 | NA | 0.072 | NA |
| 0.05M $CaCl_2$ | 4.34 | 293 | 1.40 | 0.75 | 0.094 | NA |
| 0.075M $CaCl_2$ | 7.70 | 520 | 2.48 | 0.93 | 0.226 | NA |
| 0.10M $CaCl_2$ | 9.98 | 674 | 3.22 | 1.11 | 0.293 | 0.09 |
| 0.15M $CaCl_2$ | 10.5 | 707 | 3.39 | 0.98 | 0.327 | NA |
| 0.20M $CaCl_2$ | 10.5 | 707 | 3.39 | NA | NA | NA |

*The conductivity in the CS is calculated to correspond to about 0.1M NaCl.
NA: not analysed Conclusion:

Calcium chloride can be used as an effective releaser of FVIII. The optimal release condition seems to be about 0.1 M $CaCl_2$. In comparison with NaCl, the $CaCl_2$ release procedure seems to produce a purer harvest with higher quality. The DNA release from the cells is significantly decreased (a factor 10) when using the calcium chloride release method compared with the high (0.55 M) NaCl release method. This is a very interesting feature of calcium chloride, as the removal of DNA in the product is an important issue from a purification point of view when working with recombinant produced pharmaceuticals. The regulatory demand of DNA content in the final product is set very low, to protect unwanted transmissions. Thus a low DNA release harvest procedure is a highly interesting property of the method of the invention.

Example 10

Cultivation in Pilot Scale, NaCl/$CaCl_2$/H is FVIII Release, Capture Step 9844 g of CS9 (sample 1), $2.4 \times 10^6$ cells/ml, (clone HEK 293T 48/9H5, vector pTGF8-3)) was filtered through a 0.5 µm profile filter (0.6 $m^2$). The filter (with the removed cells) were then washed with 7.5 L of a solution of 0.55 M NaCl+10 mM $CaCl_2$+10 mM Histidin, pH 7, to release any adhering FVIII. The filtrate and the wash were pooled (sample 2). Before use, the filter had been washed with 12 Ll of distilled water and equilibrated with 2 l of a buffer containing 100 mM NaCl+10 mM $CaCl_2$+10 mM histidine pH 7. The filtration was performed with a trans membrane pressure of 0.2 bar. About half of the filtrate (47%) was used for further processing to the capture step (anion chromatography exchanger), the material was diluted to a final conductivity of 13.0 mS/cm at 25° C. before applying it to the capture step. 9317 of the starting material (sample 3) were applied to the capture step after the elution of the capture step with increased ionic strength, 3.8 g of the product was eluated (sample 4). The results are summarized in Table 19.

TABLE 19

| Sample No | (g) | FVIII (IU/ml) | FVIII, total (IU) | Yield total, (%) | Yield each step (%) |
|---|---|---|---|---|---|
| Sample 1 (CS) | 9844 | 0.62 | 6103 | 100 | 100 |
| Sample 2 (cell filtrate) | 12276 | 1.13 | 13845 | 226 | 226 |
| Sample 3 (capture start) | 9317 | 0.68 | 6336 | 226 | 100 |
| Sample 4 (capture eluat) | 318 | 14.0 | 4452 | 146 | 70 |

Conclusion:

The example shows a different way of using the invention; the release substance (0.55 M NaCl) is added after the separation of cells and cell supernatant. The advantage is a lower level of ionic strength in the recovered solution after filtration. The lower ionic strength might be of importance if the solution is to be further purified on a ion-exchange based capture step. A ionexchanger can not be processed with a to high ionic strength. In that protein solution must be diluted, which can have certain practical disadvantages due to large volumes after dilution. Thus the described release procedure minimizes the dilution volume before the capture step. The described procedure in liter scale increased the FVIII recovery about 2 times (compared with untreated c). The cell suspension media could successfully be removed using an anion chromatography exchanger, which also reduced the volume with a factor 29.

Example 11

Cultivation in Liter Scale, CaCl$_2$ Release, Capture Step 7403 g of cell suspension (sample 1 was withdrawn, centrifuged and cell free supernatant was analyzed for FVIII) containing 3×10$^6$ cells/ml, clone and vector will be included by SW was added 370 g of a 1 M CaCl$_2$ solution to a final concentration of 50 mM CaCl$_2$. The solution was stirred for 10 minutes (sample 2 was withdrawn, centrifuged and cell free supernatant was analyzed for FVIII) where after the cells were removed with filtration (0.4 m$^2$, 0.5 µm profile filter). Before use, the filter was washed with 10 l of distilled water and equilibrated with 5 l of a buffer containing 100 mM NaCl+50 mM CaCl$_2$+50 mM histidine pH 7.1. The filtration was performed with a trans membrane pressure of about 0.2 bar. After the cell suspension has been filtered, each filter was washed with 2 l of said equilibration buffer, to recover adsorbed FVIII. The filtrate and the wash was pooled (sample 3, 11856 g) and added Tween® 80 to a final concentration of 0.01% (to avoid protein adsorption during further processing).

Filtrate 1 was filtrated through a 0.2 m$^2$ 0.5 µm/0.2 µm filter to protect the capture resin in the next ion exchange step. Before use, each filter was washed with 5 l of distilled water and equilibrated with 5 l of a buffer containing 100 mM NaCl+50 mM CaCl$_2$+50 mM histidine+0.01% Tween® 80, pH 7.1. The filtration was performed with a trans membrane pressure of 0.5 bar. After that filtrate 1 has been filtered, the filter was washed with 4 l of said equilibration buffer, to recover adsorbed FVIII. The filtrate and the wash were pooled (14286 g, sample 4).

The 0.2 µm filtrate was diluted before applying to the capture step. 28613 g of the starting material (capture start; sample 5) was applied to the capture step, 580 g of the product was eluted (sample 6). The results are summarized in Table 20.

TABLE 20

| Sample No | Weight (g) | FVIII (IU/ml) | FVIII, total (IU) | Yield, total (%) | Yield each step (%) |
|---|---|---|---|---|---|
| Sample 1 (cell susp.) | 7403 | 0.32 | 2369 | 100 | 100 |
| Sample 2 (cell susp. + Ca) | 7773 | 2.8 | 21764 | 919 | 919 |
| Sample 3 (cell filtrate) | 11874 | 1.7 | 20394 | 861 | 94 |
| Sample 4 (0.2 um filtrate) | 14286 | 1.39 | 19905 | 840 | 98 |
| Sample 5 (capture start) | 28613 | 0.61 | 17454 | 737 | 100 |
| Sample 6 (eluat) | 580 | 22.8 | 13224 | 558 | 76 |

Conclusion:

The release procedure of the invention, using a release composition of 50 mM CaCl$_2$, 50 mM histidine and 100 mM NaCl in pilot scale, increased the FVIII recovery with about 9 times compared with untreated CS. The cell suspension media could successfully be removed using an anion chromatography exchanger as a capture step, which reduced the volume with a factor 50.

Example 12

Increase (0.4 M NaCl) and Decrease (0.1 M NaCl) of Salt Content During Cultivation A very important feature of the invention would be if it were possible to use it in cycles during cultivation. This would significant increase the recovery and the productivity of the cell line. Below this idea has been tested with promising results.

A (0.4 M NaCl Cultivation):

To CS11 (1.8 ml) containing 2.8×10$^6$ cells/ml (clone HEK 293T 48/9H5, vector pTGF8-3)), which had been cultivated as described in Example 1, 0.32 ml of 2.1 M NaCl was added (final concentration 0.4 M NaCl). The solution was mixed for 15 minutes, where after the suspension was carefully centrifuged (60×g), the cell supernatant was withdrawn and analysed with regard to FVIII:C, the remaining cells where then dissolved in the cultivation media back to the normal salt content (about 0.1 M NaCl). The cell suspension was allowed to grow for 3 days, where after the above procedure was repeated again, with the exception that the salt treatment duration was 2.5 h. Again the NaCl concentration was decreased due to dilution with cultivation medium to about 0.1 M. The cell suspension was again allowed to grow, this time for 4 days. Cell concentration and FVIII:C was followed during the experiment B (0.1 M NaCl Cultivation):

The experiment was performed as in A, with the exception that no NaCl was added. Thus the NaCl concentration was about 0.1 M as present in the cultivation media. The results are summarized in Table 21.

TABLE 21

| Sample | Time (hour) | Cell conc. (10$^6$) | FVIII:C (IU/ml) |
|---|---|---|---|
| A CS 0.4M | 0 | 2.8 | 1.4 |
| B CS 0.1M | 0 | 2.8 | 0.3 |
| A CS 0.4M | 20 | 0.1 | NA |
| B CS 0.1M | 20 | 0.2 | 0.53 |
| A CS 0.4M | 70 | 0.8 | 0.24 |
| B CS 0.1M | 70 | 0.9 | NA |
| A CS 0.4M | 90 | 0.3 | NA |
| B CS 0.1M | 90 | 0.4 | NA |
| A CS 0.4M | 110 | 0.5 | NA |
| B CS 0.1M | 110 | 1.1 | NA |
| A CS 0.4M | 145 | 1.0 | NA |
| B CS 0.1M | 145 | 1.3 | NA |
| A CS 0.4M | 165 | 2.2 | NA |
| B CS 0.1M | 165 | 2.7 | NA |

NA: not analysed.

Conclusion:

The results shows that the cells which has been treated with short pulses of 0.4 M NaCl, seems to initially grow a little bit slower. However, after 165 hours there is no significant difference between the high salt treatment and the reference. In conclusion, to use short periods of increased salt concentrations according to the invention, seems to be an interesting possibility.

Example 13

Production Scale, CaCl$_2$/Histidine/NaCl FVIII Release Composition Capture Step 150 kg CS12 (sample 1 was withdrawn, centrifuged and cell free supernatant was analyzed for FVIII) containing 0.8× 10$^6$ cells/ml, (clone HEK 293T 48/9H5, vector pTGF8-3) was added 16.7 kg of a 0.5 M CaCl$_2$ solution, to a final concentration of 50 mM CaCl$_2$. The solution was stirred for 15 minutes (sample 2 was withdrawn, centrifuged and cell free supernatant was analyzed for FVIII) where after the cells were removed with filtration (7 m$^2$, 0.5 µm profile filter). Before use, the filters had been washed with 400 l of distilled water and equilibrated with 300 l of a buffer containing 100 mM NaCl+50 mM CaCl$_2$+50 mM histidine pH 7.1. The filtration was performed with a trans membrane pressure of about 0.2 bar. After the cell suspension has been filtered the filters were washed with 2×100 l of said equilibration buffer, to recover adsorbed FVIII. The filtrate and the wash were pooled (sample 3, 359 kg). and added Tween® 80 to a final concentration of 0.01% (to avoid protein adsorption during further processing).

The Tween® added filtrate (sample 3) was filtrated through a 0.6 m$^2$ 0.5 µm/0.2 µm filter to protect the capture step. Before use, the filter was washed with 50 l of distilled water and equilibrated with 50 l of a buffer containing 100 mM NaCl+50 mM CaCl$_2$+50 mM histidine+0.01% Tween® 80, pH 7.1. The filtration was performed with a trans membrane pressure of about 0.5 bar. The filter was washed with 30 l of equilibration buffer, to recover adsorbed FVIII. The filtrate and the wash was pooled (38 kg, sample 5).

The 0.2 µm filtrate was diluted before applying to the capture step 774 kg of the starting material (capture start, sample 5) were applied to the capture anion exchanger 4.68 kg was eluted (sample 6). The results are summarized in Table 22.

TABLE 22

| Sample No | Weight (kg) | FVIII:C (IU/ml) | FVIII, total (kIU) | Yield total, (%) | Yield each step (%) |
|---|---|---|---|---|---|
| Sample 1 (cell susp.) | 150 | 0.75 | 112 | 100 | 100 |
| Sample 2 (cell susp. + Ca) | 168 | 5.1 | 857 | 765 | 765 |
| Sample 3 (cell filtrate) | 359 | 2.9 | 1041 | 929 | 929 100 |
| Sample 4 (0.2 µm filtrate) | 384 | 2.8 | 1075 | 960 | 97 100 |
| Sample 5 (capture start) | 774 | 1.3 | 1006 | 898 | 94 100 |
| Sample 6 (capture eluat) | 4.680 | 195 | 913 | 815 | 91 |

Conclusion:

The performance of the release procedure, using 50 mM CaCl$_2$, 50 mM histidine and 100 mM NaCl is not scale dependent. The FVIII recovery increases with more than 9 times for a batch size of 150 kg. In addition, the resulting FVIII solution could be further concentrated through a capture anion exchanger. The volume reduction factor over the capture step was 165 times and the process time was about 4 h.

Example 14

FVIII Release as a Function of Cell Concentration Using 0.1 M and 0.5 M NaCl

During cell cultivation, performed as described in example 1, samples from CS13 (clone HEK 293T 48/9H5, vector pTGF8-3) were withdrawn regularly. Cells where counted and the CS sample was divided in two tubes. In one of the tubes a stock solution of 1 M NaCl was added 1+1 to the CS, to a final concentration of 0.5 M. The sample was incubated for 15 minutes where after the tubes were centrifuged at 2500 r/min for 1 minute to remove the cells and the cell supernatant was analyzed for FVIII:C activity. The results are summarized in Table 23.

TABLE 23

| Time (h) | Viable cells, (10$^4$/ml) | FVIII:C × 10$^{-6}$/cell, low salt content (0.1M NaCl) | FVIII:C × 10$^{-6}$/cell, high salt content (0.5M NaCl) |
|---|---|---|---|
| 0 | 9.7 | NA | NA |
| 26 | 15.0 | 0.5 | 1.8 |
| 70 | 13.4 | 0.2 | 1.0 |
| 93 | 37.2 | 0.8 | 1.7 |
| 141 | 51.0 | 0.9 | 2.4 |
| 163 | 85.0 | 1.0 | 2.9 |
| 192 | 157 | 0.4 | 2.5 |
| 215 | 118 | 0.4 | 3.1 |

NA: not analyzed.

Conclusion:

The example shows clearly that FVIII is bound to the surfaces on the cell during cell cultivation. The level of FVIII within the low salt harvest is almost unchanged when the cell concentration increases. Whereas within the high salt harvest, FVIII increase follow the increase in cell concentration, as expected, if no or minor interaction with the cell membrane occurs.

Example 15

Stability of FVIII Containing Cell Supernatant with Different Calcium Concentration A cell suspension (CS14) cultivated according to example 1 (clone HEK 293T 48/9H5, vector pTGF8-3), was harvested separating the cells with centrifugation. The cell free supernatant (pH 7) was added different amounts of calcium chloride. The solution was stored in room temperature and samples were withdrawn and frozen −70° C. after 0, 6 and 24 h. The FVIII stability was followed analyzing FVIII:C. The results are summarized in Table 24.

TABLE 24

| Addition | 0 h | 6 h | 24 h | 48 h |
|---|---|---|---|---|
| 0 mM calcium | 100% | 95% | 67% | 48% |
| 2 mM calcium | 100% | 89% | 92% | 85% |
| 10 mM calcium | 100% | 95% | 101% | 93% |
| 50 mM calcium | 100% | 98% | 100% | 97% |

Conclusion:

Calcium has a stabilizing effect on FVIII in cell supernatant medium. It is known in the literature that calcium is an important component for the structure, function and stability of FVIII in the range 1-50 mM (Wang et al., International Journal of Pharmaceutics 259 (2003) 1-15). Thus, the use of calcium chloride as a release substance for FVIII, according to the invention has double effects: releasing substance and stabilizing of FVIII.

Moreover, as can be seen from Western blot analysis in FIG. 3B, no significant change could be detected in the molecular mass distribution of crude FVIII, using different release substances of the invention and compared with normal harvest conditions (about 0.1 M NaCl).

Example 16

Production of Cell Lines for an Adsorption Study

In the following examples 16 to 20 an adsorption study is provided where FVIII was added to mock (=cells without FVIII production capacity) HEK-293F cells and also BHK cells. The result of these experiments shows that after addition of FVIII to the cell suspension, the amount of FVIII in the cell supernatant decreased with time, indicating adsorption to the cell surface. An identical experiment, with the exception that IgG was used instead of FVIII, was performed with the HEK-293F cells. This experiment showed that IgG did adsorb to the HEK 293F cells cultivated under serum free conditions.
Cell Line:

The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.
Normal Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the poly-adenylation site provide high-level recombinant protein production. The resistance against two antibiotics provides an efficient tool for clone selection after transfection. To be able to produce host cell proteins without FVIII (for development of antibody based analytical method for host cell proteins) a so-called mock cell line was produced where the FVIII gene was excluded out from the plasmid. This non FVIII producing cell line was also used for FVIII (and IgG) adsorption studies.
Cultivation:

Static cultivation of cells was done in TC-flasks of different size. All medium used was serum free. Bottles were used for dynamic cultivation. For agitation purpose the bottles where placed on a horizontal shaker situated within the incubator. All incubators were set to 5% carbon dioxide, 37° C. and 95% relative humidity.
Description of Analysis:
Factor VIII:C Screening Method Based on Coatest:

The method is based on the two-stage principle, and was performed using micro plate technique. In stage one, activated factor X (Xa) is generated via the intrinsic pathway where factor VIII: C acts as a co-factor. In stage two, Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated.
IgG Elisa:

The IgG concentrations were determined with an ELISA-method, Mouse-IgG ELISA (Roche Applied Science, Germany), according to the manufacturer's instructions. A special catching antibody is bound adsorptively to the wells of microplates. After blocking with Blocking reagent the antibody contained in the sample (e.g., hybridoma-supernatant, ascites dilution, etc.) is bound to the capture antibody during a further incubation step. POD is fixed to the monoclonal antibody using a POD-labeled, balanced mixture of anti-mouse- and anti-mouse-antibodies (immunosorbed Fab-fragments). With the highly sensitive ABTS-perborate system a dark green color is formed in the reaction with the fixed peroxidases. Evaluation is performed using a standard graph.

Example 17

Production of a Laboratory Sample of a B-Domain Deleted FVIII in HEK 293F Cell Line Cell Line:

The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.
Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the poly-adenylation site provide high level recombinant protein production. The resistance against two antibiotics provides an efficient tool for clone selection after transfection.
Transfection:

Immediately following revitalization, adherent 293F cells were transfected with pcDNA3.1 using the calcium phosphate method (C. Chen et al., Mol. Cell. Biol. 7(8), 2745-2752 (19887)). Selection with hygromycin (200 ng/ml) started 72 h after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clone No. 293F 4/24K.

Cultivation:

Static cultivation of cells was done in TC-flasks of different size. All medium used was serum free. Bottles and up to 100 L bioreactors were used for dynamic cultivation. For agitation purpose the bottles where placed on a horizontal shaker situated within the incubator. All incubators were set to 5% carbon dioxide, 37° C. and 95% relative humidity.

Example 18

Adsorption of FVIII to Serum Free Cultivated HEK 293F Cells

A HEK 293F cell suspension was cultivated under serum free conditions according to example 16. FVIII was added as described in Table 25 and the cell suspension ($1 \times 10^6$ cells/ml) was cultivated as before, sample of cell free supernatant was taken after 1, 5 and 24 h (controls of respectively FVIII solution added to medium without cells and incubated under the same conditions as the cell suspension, were taken at the same time). Samples where frozen and analysed for FVIII:C activity. The results are summarized in Table 26.

TABLE 25

| FVIII addition | Type of factor |
|---|---|
| A, 100 IU/ml | Full length plasma derived FVIII stabilised with vWf* |
| B, 100 IU/ml | B-domain deleted recombinant FVIII** |

*Octanate ® (Octapharma)
**A laboratory sample of B-domain deleted FVIII, purity 90%, no vWf content, cultivated according to example 17

TABLE 26

| FVIII | FVIII:C [IU/ml] | Change* |
|---|---|---|
| A, 1 h | 50.1 | 7.5% |
| A, 5 h | 48.5 | 4.0% |
| A, 24 h | 27.4 | −41.4% |
| B, 1 h | 27.6 | 6.4% |
| B, 5 h | 15.0 | −42.2% |
| B, 24 h | 8.5 | −48.3% |

*After compensation with control

Conclusion:

FVIII adsorbs to cell surface under cultivation premises. Tendency that recombinant B-domain deleted FVIII adsorbs faster compared to full-length plasma FVIII stabilised with von Willebrandt factor.

Example 19

Adsorption of FVIII to BHK Cells

ABHK-21 cells (ATCC 13001) where cultivated on Cytodex-3 in 250 ml spinner flask (Corning). The medium used was D-MEM with 10% FBS. Before use, the cell supernatant was exchanged with 3 volumes of serum free buffer (PBS-A with 0.03% w/w EDTA) to remove the serum components. FVIII was added as described in Table 27 and the cell suspension ($1.5 \times 10^6$ cells/ml) was cultivated as before, sample of cell free supernatant was taken after 1, 5 and 24 h (controls of respectively FVIII solution added to medium without cells and incubated under the same conditions as the cell suspension, were taken at the same time). The results are summarized in Table 28.

TABLE 27

| FVIII addition | Type of factor |
|---|---|
| A, 100 IU/ml | Full length plasma derived FVIII stabilised with vWf* |

*Octanate ® (Octapharma)

TABLE 28

| FVIII | FVIII:C [IU/ml] | Change* |
|---|---|---|
| A, 1 h | 50.6 | 8.4% |
| A, 5 h | 45.6 | −2.3% |
| A, 24 h | 30.1 | −35.5% |

*After compensation with control

Conclusion:

FVIII adsorbs to BHK cell surface under cultivation premises.

Example 20

Adsorption of IGG to Serum Free Cultivated HEK 293F Cells

A HEK 293F cell suspension was cultivated 6 days under serum free conditions according to example 16. To the cells ($0.9 \times 10^6$ cells/ml) different amounts of IGG (lyophilised IgG standard (Roche Diagnostics) diluted in PBS to three different solutions of 10300, 1030, and 103 ng/ml). The different IgG stem solutions were portioned out into micro tubes and one part (0.25 ml) of these standard solutions were mixed with one part (0.25 ml) of the resuspended cells. This led to a 2-fold dilution of the IgG standards and therefore the expected IgG concentrations was 5150, 515 and 51.5 ng/ml. As positive controls, one part of each IgG standard solution was mixed with one part of culture medium and as negative controls one part of the resuspended cells was mixed with one part of pure PBS-A, containing no IgG. After 1 h of incubation the samples were centrifuged at 6000 rpm and the supernatants were collected and analysed. Sample experiments were repeated 6 times and control experiments were repeated at least 9 times. Samples where frozen and analysed for IGG content.

Results:

An overview of the results of the experiments where IgG standards of three different concentrations where incubated together with HEK cells is presented in Tables 29 and 30. Even though the accuracy of the result after incubation with 5150 ng/ml standard solution is not adequate, −5.02±20.0%, all results show a decrease in IgG concentration after incubation. With the other two standard solutions, 515 and 51.5 ng/ml, the decrease was −26.0±9.10% and −15.8±11.5% respectively. This reduction of IgG in the sample supernatants, compared to the positive controls, indicates that IgG has adsorbed to HEK cells.

TABLE 29

Mean IgG concentrations and standard deviations for controls and samples in adsorption experiments. Three different IgG concentrations (5150 ng/ml, 515 ng/ml and 51.5 ng/ml) were incubated together with fresh medium (in controls) and HEK suspension containing $0.9 \times 10^6$ HEK cells/ml (in samples).

| | IgG conc. before incubation [ng/ml] | Mean IgG conc. after incubation, μ [ng/ml] | Standard dev. |
|---|---|---|---|
| Positive controls: (no cells) | 5150 | 4860 | 945 |
| | 515 | 619 | 59.1 |
| | 51.5 | 49.7 | 5.57 |
| Negative controls: ($0.9 \times 10^6$ cells/ml) | 0 | <7.00 | — |
| Samples: ($0.9 \times 10^6$ cells/ml) | 5150 | 4610 | 337 |
| | 515 | 458 | 30.6 |
| | 51.5 | 41.9 | 4.98 |

TABLE 30

95% confidence intervals for $\mu_s - \mu_c$, where $\mu_s$ is the mean IgG concentration in the samples and $\mu_c$ is the mean IgG concentration in the controls for each stem solution respectively.

| IgG concentration before incubation | 95% conf. interv. for $\mu_s - \mu_c$ | | Change in amount of IgG per cell |
|---|---|---|---|
| [ng/ml] | [ng/ml] | [%] | [pg/cell] |
| 5150 | −244 ± 970 | −5.02 ± 20.0 | −0.542 ± 2.17 |
| 515 | −161 ± 56.3 | −26.0 ± 9.10 | −0.357 ± 0.124 |
| 51.5 | −7.85 ± 5.72 | −15.8 ± 11.5 | −0.0174 ± 0.0131 |

Conclusion:

IGG binds to HEK 293 Cells cultivated under serum free conditions.

Example 21

Production of Expression Cell Line

Cell line: The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.

Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the poly-adenylation site provide high level recombinant protein production. The resistance against two antibiotics provides an efficient tool for clone selection after transfection.

Transfection:

Immediately following revitalization, adherent 293F cells were transfected with pcDNA3.1 using the calcium phosphate method (C. Chen et al., Mol. Cell. Biol. 7(8), 2745-2752 (19887)). Selection with hygromycin (200 ng/ml) started 72 h after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clone No. 293F 4/24K.

Cultivation:

Static cultivation of cells was done in TC-flasks of different size. All medium used was serum free. Bottles and up to 100 L bioreactors were used for dynamic cultivation. For agitation purpose the bottles where placed on a horizontal shaker situated within the incubator. All incubators were set to 5% carbon dioxide, 37° C. and 95% relative humidity.

Cell Suspension:

The starting material for harvest experiments is the cell suspension (hereinafter shortly referred to as "CS".). Before use, the cell suspension has been induced with sodium butyrate for at least one day, to improve the productivity of the cells.

Description of Analysis, Factor VIII: C, Screening Method Based on Coatest:

The method is based on the two-stage principle, and was performed using micro plate technique. in stage one, activated factor X (Xa) is generated via the intrinsic pathway where factor VIII: C acts as a co-factor. In stage two, Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated.

Example 22

Harvest Using Different Concentration of Peptone

Different amounts of solid peptone (Soy Peptone A2 SC 19649, Organo Technie, La Courneuve, France) or salts (see, Table 31) were added to 10 ml of a cell suspension ($2.0 \times 10^6$ cells/ml). The cells had been cultivated as described in example 21 and were withdrawn before harvest. The washing substances were dissolved and the suspension was gently mixed (using a rocking mixer) for 1 h at room temperature (21° C.), using 15 ml tubes. The tubes were then centrifuged at 600 r/min for 5 min to remove the cells, where after the cell supernatant was analysed for FVIII:C activity. The results are summarized in Table 31.

TABLE 31

| Wash concentration | FVIII:C [IU/ml]* | FVIII release [IU FVIII:C × $10^{-6}$/cell]* |
|---|---|---|
| Reference, untreated | 1.1 | 0.55 |
| 0.5M NaCl | 6.7 | 3.35 |
| 50 mM CaCl$_2$ | 7.6 | 3.78 |
| 0.5M NaCl + 50 mM CaCl$_2$ | 8.5 | 4.25 |
| 2.5% Peptone | 2.0 | 1.00 |

TABLE 31-continued

| Wash concentration | FVIII:C [IU/ml]* | FVIII release [IU FVIII:C × $10^{-6}$/cell]* |
|---|---|---|
| 5% Peptone | 3.3 | 1.65 |
| 10% Peptone | 5.9 | 2.95 |
| 20% Peptone | 6.7 | 3.35 |

*Compensated for dilution factors

Conclusion:

Increase of sodium chloride and or calcium chloride or peptone concentration before the harvest significant increase the recovered FVIII compared with untreated sample.

Example 23

Cultivation with and without Low Amount of Peptone and Thereafter Addition of Low Concentration Peptone to Study FVIII Release Under Conditions Which can be Used During Cultivation Two different cultivated cell suspensions was used in this experiment, both containing 5 mg/ml insulin (Monotard®, Novo Nordisk) and one also containing 0.2% peptone in the serum free cultivation medium from start. Otherwise the cell suspension was cultivated as described in example 21.

Different amounts of peptone (Soy Peptone A2 SC 19649, Organo Technie, La Courneuve, France) or $CaCl_2$ (namely a 0.5 M solution of $CaCl_2$ to reach a final concentration of 50 mM $CaCl_2$; see table 32) were added to 5 ml of cell suspension ($1.62 \times 10^6$ cells/ml for cell suspension cultivated without peptone and $1.38 \times 10^6$ cells/ml for cell suspension cultivated with 0.2% peptone) The added peptone was a 10% solution dissolved in cultivation medium (with the exception for the 18% peptone experiment in which the peptone was added as solid). After addition of release substances, the suspension was gently mixed (using a rocking mixer) for 1 h at room temperature (21° C.) using 15 ml tubes. The tubes were then centrifuged at 600 r/min for 5 min to remove the cells, where after the cell supernatant was analysed for FVIII:C activity. The results are summarized in Table 32.

TABLE 32

| Added amount of release component at time for harvest | FVIII:C × $10^{-6}$/ cell (cultivated with 0.2% peptone)* | FVIII:C × $10^{-6}$/ cell (cultivated with 0% peptone)* |
|---|---|---|
| 0 (reference, untreated) | 0.51 | 0.40 |
| 0.2% peptone | 0.51 | 0.41 |
| 0.9% peptone | 0.54 | 0.52 |
| 1.7% peptone | 0.70 | 0.50 |
| 2.9% peptone | 0.72 | 0.53 |
| 18% peptone (high conc. ref.) | 1.71 | 1.57 |
| 50 mM $CaCl_2$ (salt reference) | 1.62 | 1.84 |

*Compensated for dilution factors

Conclusion:

Cultivation with low amounts peptone releases more FVIII from the cell surface compared with cultivation without any added peptone (see sample reference, untreated). This is also valid when small amount of peptone is added 1 h before the harvest. Thus, peptone contributes to the release of FVIII from the cell surface even in relative low concentrations which can be used during the cultivation process without negative effect towards the cells.

Sequence Listing, Free Text

SEQ ID NO:1: DNA sequence of human factor VIII.
SEQ ID NO:2: Amino acid sequence of human factor VIII.
SEQ ID NO:3: DNA sequence of vector pTGF8-3.
SEQ ID NO:4: Amino acid sequence of B-domain deleted factor VIII as encoded by pTGF8-3.
SEQ ID NO:5: DNA sequence of vector pTGF8-2hyg-s.
SEQ ID NO:6: Amino acid sequence of B-domain deleted factor VIII as encoded by pTGF8-2hyg-s.
SEQ ID NOs: 7 to 9: Linker peptides.
SEQ ID NO: 10: DNA sequence of vector pTGF36.
SEQ ID NO:11: Amino acid sequence of human factor IX as encoded by pTGF36.

The invention claimed is:

1. A method for the recombinant production of at least one target protein in eukaryotic cells, which comprises effecting cultivation of eukaryotic cells, being capable of expression of said at least one target protein, under protein-free conditions and subjecting a suspension of said cells, prior to separation of the protein from the cells, to a non-physiologically increased concentration of at least one ionic substance selected from the group consisting of $NH_4$Acetate, $MgCl_2$, $KH_2PO_4$, $Na_2SO_4$, KCl, an amino acid with a charged R-group is a basic amino acid selected from the group consisting of arginine, histidine and lysine, and a peptone; and wherein:
   (i) KCl is added to raise its concentration in the cell suspension to at least 0.2 M;
   (ii) lysine is added to raise its concentration in the cell suspension to at least 0.2 M;
   (iii) arginine is added to raise its concentration in the cell suspension to at least 0.2 M;
   (iv) histidine is added to raise its concentration in the cell suspension to at least 0.01 M;
   (v) peptone is added to raise its concentration in the cell suspension to at least 0.01% (w/w);
   (vi) $NH_4$Acetate is added to raise its concentration in the cell suspension to at least 0.5 M;
   (vii) $MgCl_2$ is added to raise its concentration in the cell suspension to at least 0.5 M;
   (viii) $KH_2PO_4$ is added to raise its concentration in the cell suspension to at least 0.5 M; and/or
   (ix) $Na_2SO_4$ is added to raise its concentration in the cell suspension to at least 0.5 M.

2. The method of claim 1, wherein the adjusting of the concentration of the cell suspension is effected by adding to the cell suspension a release composition comprising said at least one ionic substance said release composition
   (i) being added to the cell suspension in solid or liquid form; and/or
   (ii) being added to the cell suspension up to 3 days prior to the separation of the protein; and/or
   (iii) being added to the cell suspension at the start and kept constant during continuous cultivation and harvest of the protein; and/or
   (iv) being added to the cell suspension during harvest periods and in between exchanged with physiological conditions, during the continuous cultivation and harvest process of the protein; and/or
   (v) being directly added to the culture broth or being added to the cells or a suspension of the cells isolated from the culture broth; and/or
   (vi) being gradually added to reach the final concentration within 1-2000 minutes; and/or
   (vii) being added with diafiltration technique.

3. The method of claim 1, wherein
(i) the target protein(s) is/are selected from plasma proteins, peptide hormones, growth factors, cytokines and antibodies, wherein the proteins are plasma proteins are selected from human and animal blood clotting factors including fibrinogen, prothrombin, thrombin, FX, Fa, FIX, FIXa, FVII, FVIIa, FVIII, FVIIIa, FXI, FXIa, FXII, FXIIa, FXIII and FXIIIa, muteins of clotting factors, von Willebrand factor, transport proteins including albumin, transferrin, ceruloplasmin, haptoglobin, hemoglobin and hemopexin, protease inhibitors including β-antithrombin, α-antithrombin, α2-macroglobulin, Cl-inhibitor, tissue factor pathway inhibitor (TFPI), heparin cofactor II, protein C inhibitor (PAI-3), Protein C and Protein S, antiangionetic proteins including latent-antithrombin, highly glycosylated proteins including α-1-acid glycoprotein, antichymotrypsin, inter-α-trypsin inhibitor, α-2-HS glycoprotein and C-reactive protein and other proteins including histidine-rich glycoprotein, mannan binding lectin, C4-binding protein, fibronectin, GC-globulin, plasminogen, blood factors such as erythropoeitin, interferon, tumor factors, tPA, gCSF and derivatives and muteins thereof, domain deleted factor VIII protein, and a factor VIII mutein having SEQ ID NO:4 or 6; and/or
(ii) the eukaryotic cells are isolated cells or isolated tissue cells of invertebrates, including insects and worms, of plants, and cells of lower eukaryotes including yeast, of vertebrates, including mammals and fish including human cell and rodent cells, immortalized human fetal kidney cells including HEK293 deposited with the ATCC receiving the ATCC accession number CLR-1573, HEK293 T deposited with the DSM and receiving the DSM accession number ATCC 2494, 293 H and 293 freestyle 293 F cells, or is a CHO, Cos, hybridoma, myeloma such as NS0 cell; and/or
(iii) the mammalian cells are stably transfected with an expression cassette carrying the gene coding for the target protein(s); and/or
(iv) the ionic substance(s) is/are added to reach the equilibration balance within protein and cell surface, enough to disrupt the ionic binding and release bound proteins from the cell surface without destroying the cell; and/or
(v) at least one or more, two or more, or three or more ionic substance, is/are added; and/or
(vi) no or only small amounts of non-ionic detergents are added to the suspension and/or are present in an ionic release composition; and/or
(vii) the least one ionic substance further comprises a buffering substance to stabilize the pH; and/or
(viii) the pH of the cell suspension when subjected to the increased concentration of the at least one ionic substance is preferable in the range of stability for the selected protein, for FVIII it is from about 6.0 to 7.5; and/or
(ix) by harvesting of the protein the viability of the cells is maintained, and after harvest the non naturally increased concentration of the ionic substance is reduced or the cells are transferred into fresh culture medium, to enable a continuous cyclic production process of the protein using the same cells; and/or
(xi) the ionic release composition is selected to contain at least one substance aimed to stabilize the released proteins.

4. The method of claim 1, which comprises one or more of the following steps:
(a) cultivating the cells in a culture medium;
(b) separating the culture medium from the cultivated cells, resulting in two separate fractions, a fraction of cultivated cells and a fraction of liquid medium;
(c) contacting or suspending the fraction of cultivated cells with a release composition comprising a non-physiologically increased concentration of at least one ionic substance selected from $NH_4Acetate$, $MgCl_2$, $KH_2PO_4$, $Na_2SO_4$, KCl, an amino acid with a charged R-group is a basic amino acid selected from the group consisting of arginine, histidine and lysine, and a mixture of peptides and/or amino acids;
(d) removing the culture medium from the cells, resulting in two separate fractions, a fraction of cells and a fraction of release composition;
(e) isolating the recombinant protein from the fraction of the release composition; and
(f) suspending the fraction of cells of (d) above in culture medium and reculture.

5. The method of claim 4, wherein
(i) the cultivation of the cells is effected in suspension culture or adherent culture;
(ii) the separation of the medium from the cultivated cells in steps (b) and (d) is effected by centrifugation, filtration, diafiltration, tangential filtration, dead end filtration, micro filtration, electrical fields, magnetic fields and ultra filtration; and/or
(iii) the isolation of the protein from the medium and its purification is effected by using at least one technique selected from immuno-affinity chromatography, affinity chromatography, protein precipitation, buffer exchanges, ionic exchange chromatography, hydrophobic interaction chromatography, mixed mode hydrophobic/ion exchange chromatography media, chelating chromatography, carbohydrate affinity like lectin or heparin affinity chromatography, size-exclusion chromatography, electrophoresis, dialysis, different precipitation agents such as polyethylene glycol, ammonium sulphate, ethanol, hydroxy apatite adsorption, filter membrane adsorption, ligands coupled to magnetic particles; and/or
(iv) the carrier used for the chromatography purification, is selected from resins, particles, beads, membranes, hollow fiber or similar; and/or
(v) the isolation of the protein comprises a capture step, where the product is bound and cell cultivation media and release composition is washed away; and/or
(vi) steps (d) and (e) are effected by mixing the cell suspension with a chromatographic medium which binds the product and thereafter the chromatography media is removed from the cell suspension, using centrifugation, filtration, dead end filtration, tangential filtration, micro filtration, electrical fields, magnetic fields and/or ultra filtration.

6. The method of claim 1,
(i) which is performed under sterile conditions; and/or
(ii) wherein the medium and/or the purified protein is subjected to a virus inactivation and/or removal step.

7. The method of claim 1, wherein
(i) two or more ionic substances are mixed to form an ionic release composition; and/or
(ii) the concentration of a mixture of ionic substances needed to reach the desired release of proteins is determined by dividing the theoretic amount of ionic substances, being based on the optimal release concentration for each ionic release substance when used separately, with the number of substances; and/or
(iii) by a combination of ionic substances, due to combinatorial effects of the different ionic substances, a lower amount of each ionic substance is required to achieve the protein releasing properties of the composition and to provide simultaneously acceptable cultivation conditions for the cells; and/or (iv) the ionic release composition is selected so that at least one component acts as an stabilizer for the released protein being active before and/or after the separation of protein and cells.

8. The method of claim 7, wherein the at least one ionic substance comprises
(i) KCl; and/or
(ii) arginine, histidine or lysine.

9. The method of claim 1, wherein the cell suspension is processed with a micro filtration system where the pore in the filter has been chosen to retain the cells and the filtration technique being chosen from dead-end or tangential flow filtration techniques, and wherein a release composition is applied to the cells immediately or with a gradual increase using the diafiltration technique and the cell free product is recovered in the filtrate of said micro filtration system.

10. The method of claim 2, wherein said release composition being added 1 to 24 h prior to the separation of the protein.

11. The method of claim 2, wherein said release composition being added 1 to 120 min prior to the separation of the protein.

12. The method of claim 3, wherein
(i) the target protein(s) comprise a factor VIII mutein having SEQ ID NO:4 or 6; and/or
(ii) the eukaryotic cells are isolated cells or isolated tissue cells including HEK293 deposited with the ATCC receiving the ATCC accession number CLR-1573, HEK293 T deposited with the DSM and receiving the DSM accession number ATCC 2494, 293 H and 293 freestyle 293 F cells, or is a CHO, Cos, hybridoma, myeloma such as NS0 cell; and/or
(iii) the mammalian cells are stably transfected with an expression cassette carrying the gene coding for the target protein(s); and/or
(iv) in the ionic substance(s) the amino acid is lysine, histidine or arginine, and the peptone is a soy peptone; and/or
(v) the ionic substance(s) is/are added to reach the equilibration balance within protein and cell surface, enough to disrupt the ionic binding and release bound proteins from the cell surface without destroying the cell; and/or
(vi) at least three ionic substance are added; and/or
(vii) the release composition is free of non-ionic detergents; and/or (viii) the least one ionic substance further comprises a buffering substance selected from Goods buffer substances, including HEPES, MES and TRIS; and/or (ix) the pH of the cell suspension when subjected to the increased concentration of the at least one ionic substance is preferable in the range of stability for the selected protein, for FVIII it is from about 6.0 to 7.5; and/or (x) by harvesting of the protein the viability of the cells is maintained, and after harvest the non naturally increased concentration of the ionic substance is reduced or the cells are transferred into fresh culture medium, to enable a continuous cyclic production process of the protein using the same cells; and/or (xi) the ionic release composition is selected to contain at least one substance aimed to stabilize the released proteins.

13. The method of claim 1, wherein:
(i) KCl is added to raise its concentration in the cell suspension to a concentration ranging from 0.2 to 2 M; and/or
(ii) lysine is added to raise its concentration in the cell suspension to a concentration ranging from 0.4 to 1 M; and/or
(iii) arginine is added to raise its concentration in the cell suspension to a concentration ranging from 0.4 to 1 M; and/or
(iv) histidine is added to raise its concentration in the cell suspension to a concentration ranging from 0.05 to 0.3 M; and/or
(v) a peptone is added to raise its concentration in the cell suspension to a concentration ranging from 0.1 to 20% (w/w).

14. The method of claim 1, wherein:
(i) KCl is added to a concentration of about 0.5 M; and/or
(ii) lysine is added to raise its concentration in the cell suspension to a concentration of about 0.8 M; and/or
(iii) arginine is added to raise its concentration in the cell suspension to a concentration of about 0.8 M; and/or
(iv) histidine is added to raise its concentration in the cell suspension to a concentration of about 0.25 M; and/or
(v) a peptone is added to raise its concentration in the cell suspension to a concentration ranging from 0.1 to 20% (w/w).

15. The method of claim 5, wherein the capture step utilizes a chromatography media.

* * * * *